US008895062B2

(12) United States Patent
De Leeuw et al.

(10) Patent No.: US 8,895,062 B2
(45) Date of Patent: Nov. 25, 2014

(54) SURFACE-LAYER PROTEIN COATED MICROSPHERES AND USES THEREOF

(75) Inventors: Erik P. H. De Leeuw, Baltimore, MD (US); Wuyuan Lu, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 542 days.

(21) Appl. No.: 12/162,011

(22) PCT Filed: Jan. 24, 2007

(86) PCT No.: PCT/US2007/060962
§ 371 (c)(1),
(2), (4) Date: Dec. 9, 2008

(87) PCT Pub. No.: WO2007/087557
PCT Pub. Date: Aug. 2, 2007

(65) Prior Publication Data
US 2009/0214662 A1    Aug. 27, 2009

Related U.S. Application Data

(60) Provisional application No. 60/761,606, filed on Jan. 24, 2006.

(51) Int. Cl.
| | |
|---|---|
| *A61K 9/64* | (2006.01) |
| *A61K 31/138* | (2006.01) |
| *A61K 38/17* | (2006.01) |
| *A61K 38/16* | (2006.01) |
| *A61K 9/50* | (2006.01) |
| *A61K 47/32* | (2006.01) |
| *A61K 47/34* | (2006.01) |

(52) U.S. Cl.
CPC ........... *A61K 31/138* (2013.01); *A61K 38/1729* (2013.01); *A61K 38/164* (2013.01); *A61K 9/5052* (2013.01); *A61K 9/5068* (2013.01); *A61K 47/32* (2013.01); *A61K 47/34* (2013.01)
USPC ......................................................... 424/460

(58) Field of Classification Search
CPC .............. A61K 9/5052; A61K 38/164; A61K 38/1729; C07K 14/4723; C07K 14/335
See application file for complete search history.

(56) References Cited

U.S. PATENT DOCUMENTS

| | | | |
|---|---|---|---|
| 6,365,187 B2 | 4/2002 | Mathiowitz et al. | |
| 7,528,107 B2 * | 5/2009 | Shi et al. ............................ | 514/2 |

FOREIGN PATENT DOCUMENTS

CA      2084194      10/1992

OTHER PUBLICATIONS

Mader et al. "S-layer-coated liposomes as a versatile system for entrapping and binding target molecules," Biochimica et Biophysica Acta, 2000, 1463, 142-150.*
Navarre, W.W. and Schneewind, O. (1999) Surface proteins of gram-positive bacteria and mechanisms of their targeting to the cell wall envelope. Microbiol. Mol. Biol. Rev. 63, 174-229.
Engelhardt, H and Peters, J. (1998) Structural research on surface layers: a focus on stability, surface layer homology domains and surface layer-cell wall interactions. J. Struct. Biol. 124, 276-302.
Baumeister, W., Wildhaber, I. and Phipps, B.M. (1989) Principles of organization in eubacterial and archaebacterial surface proteins. Can. J. Microbiol 35, 215-227.
Kotiranta, A., Haapasalo, M., Kari, K., Kerosuo, E., Olsen, I., Sorsa, T., Meurman, J.H. and Lounatmaa, K. (1998) Surface structure, hydrophobicity, phagocytosis and adherence to matrix proteins of *Bacillus cereus* cells with and without the crystalline surface protein layer. Inf. Immun. 66, 4895-4902.
Thompson, S.A. (2002) Campylobacter surface-layers (S-layers) and immune evasion. Ann. Periodontol. 7, 43-53.
Sabet, M., Lee, S.W., Nauman, R.K., Sims, T. and Um, H.S. (2003) The surface (S-) layer is a virulence factor of Bacteroides forsythus. Microbiology 149, 3617-3627.
Esteve, C., Alcaide, E., Canals, E., Merino, S., Blasco, D., Figueras, M.J. and Tomas, J.M. (2004) Pathogenic *Aeromonas hydrophila* serogroup O:14 and O:81 strains with an S layer. Appl. Environ. Microbiol. 70, 5898-5904.
McCracken, V.J. and Lorenz, R.G. (2001) the gastrointestinal ecosystem: a precarious alliance among epithelium immunity and microbiota. Cell Microbiol. 3, 1-11.
Freje J., Kos, B., Svetec, I.K., Zgaga, Z., Mrsa, V. and Suskovic, J. (2005) Importance of S-layer proteins in probiotic activity of *Lactobacillus acidophilus* M92. J. Appl. Microbiol. 98, 285-292.
Horie, M., Ishiyama, A., Fujihira-Ueki, Y., Sillanpää, J., Korhonen, T.K. and Toba, T. (2002) Inhibition of the adherence of *Escherichia coli* strains to basement membrane by *Lactobacillus crispatus* expressing an S-layer. J. Appl. Microbiol. 92, 396-403.

(Continued)

*Primary Examiner* — Christina Bradley
(74) *Attorney, Agent, or Firm* — Marianne Fuierer; Moore & Van Allen, PLLC

(57) ABSTRACT

The invention provides surface-layer protein coated microspheres for delivery of a therapeutic agent to the intestine. These surface-layer protein coated microspheres generally include a core encapsulated by a microsphere which is coated by surface layer protein. The core includes a therapeutic agent, such as a defensin. The invention also includes methods of making and using the surface-layer protein coated microspheres of the invention for administering therapeutic agents to a subject in need thereof. The invention also includes pharmaceutical dosage units that include the surface-layer protein coated microspheres of the invention. The invention further includes various labeled defensins for use in the study of the properties and actions of defensins, and further includes the use of defensins, particularly HD5α in the treatment of inflammatory conditions of the bowel, such as Crohn's disease.

7 Claims, 11 Drawing Sheets

(56) References Cited

OTHER PUBLICATIONS

Hynönen, U., Westerlund-Wikström, B., Palva, A. and Korhonen, T.K. (2002) Identification by flagellum display of an epithelial cell- and fibronectin-binding function in the SlpA surface protein of *Lactobacillus brevis*. J. Bacteriol. 184, 3360-3367.

Sára, M. and Sleytr, U.B. (2000) S-layer proteins. J. Bacteriol. 182, 859-868.

Beveridge T.J., Pouwels, P.H., Sára, M., Kotiranta, A., Lounatmaa, K., Kari, K., Kerosuo, E., Haapsalo, M., Egelseer, E.M., Schocher, I., Sleytr, U.B., Morelli, M., Callegari, M.L., Nomenelli, J.F., Bingle, W.H., Smit, J., Leibovitz, E., Lemaire, M., Miras, I., Salamitou, S., Beguin, P., Ohayon, H., Gounon, P., Matuschek, M. and Koval, S.F. (1997) Functions of S-layers. FEMS Microbiol. Rev. 20, 99-149.

Rakoff-Nahoum, S., Paglino, J., Eslami-Varzaneh, F., Edberg, S. and Medzhitov, R. (2004) Recognition of commercial microflora by toll- like receptors is required for intestinal homeostasis. Cell 118, 229- 241.

Russell, M.W. and Mestecky, J. (2002) Humoral immune responses to microbial infections in genital tract. Microbes Infect. 4, 667-677.

Shikina, T., Hiroi, T., Iwatani, K., Jong, M.H., Fukuyama, S., Tamura, M., Kubo, T., Ishikawa, H. and Kiyono, H. (2004) IgA class switch occurs in the organized nasopharynz-and-gut-associated lymphoid tissue, but not in the diffuse lamina propria of airways and gut. J. Immunol 172, 6259-6264.

Neutra, M.R., Pringault, E. and Kraehenbuhl, J.P. (1996) Antigen sampling across epithelial barriers and induction of mucosal immune responses. Annu. Rev. Immunol 14, 275-300.

Janeway, C.A. Jr., and Medzhitov, R. (2002) Innate Immune Recog- nition. Annu. Rev. Immunol 20, 197-216.

Gordon, S. (2002) Pattern recognition receptors: Doubling up for the innate immune response. Cell 111, 927-930.

Akira, S. and Takeda, K. (2004) Toll-like receptor signaling. Nat. Rev. Immunol 4, 499-511.

Chamaillard, M., Girardin, S.E., Vialla, J. and Philpott, D.J. (2003) Nods, nalps and naip: intacellular regulators of bacterial induced inflammation. Cell Microbiol. 5, 581-592.

Hoffmann. J.A, Kafatos, F.C., Janeway, C.A. and Ezekowitz, R.A. (1999) Phylogenetic perspectives in innate immunity Science 284, 1313-1318.

Zhang, D., Zhang, G., Hayden, M.S., Greenblatt, M.B., Bussey, C., Flavell, R.A. and Ghosh, S. (2004) A toll-like receptor that prevents infection by uropathogenic bacteria. Science 303, 1522-1526.

Heil, F., Hemmi, H., Hochrein, H., Ampenberger, F., Kirschning, C., Akira, S., Lipford, G., Wagner, H. and Bauer, S. (2004) Species- specific recognition of single stranded RNA via toll-like receptor 7 and 8. Science 303, 1526-1531.

Alexopolou, L., Holt, A.C., Medzhitov, R. and Flavell, R.A. (2001) Recognition of double-stranded RNA and activation of NF-B by toll-like receptor 3. Nature 413, 732-738.

Hayashi, F., Smith, K.D., Ozinsky, A., Hawn, T.R., Yi, E.C., Goodlett, D.R., Eng, J.K., Akira, S., Underhill, D.M. and Aderem, A. (2001) The innate immune response to bacterial flagellin is mediated by toll-like receptor 5. Nature 410, 1099-1103.

Hemmi, H., Takeuchi, O., Kawai, T., Kaisho, T., Sato, S., Sanjo, H., Matsomoto, M., Hoshino, K., Wagner, H., Takeda, K. and Akira, S. (2000) A toll-like receptor recognizes bacterial DNA. Nature 408, 740-745.

Matsumoto, M., Funami, K., Tanabe, M., Oshiumi, H., Shingai, M., Seto, Y., Yamamoto, A. and Seya, T. (2003) Sub-cellular localization of toll-like receptor 3 in human dendritic cells. J. Immunol 171, 3154-3162.

Lund, J., Sato, A., Akira, S., Medzhitov, R. and Iwasaki, A. (2003) Toll-like receptor 9-mediated recognition of herpes simplex virus-2 by plasmacytoid dendritic cells. J. Exp. Med. 198, 513-520.

Eckmann, L. and Karin, M. (2005) NOD2 and Crohn's Disease: Loss or gain of function. Immunity 22, 661-667.

Fellerman, K., Wehkamp, J., Herrlinger, K.R. and Stange, E.F. (2003) Crohn's Disease: a defense in deficiency syndrome? Eur. J. Gastroenterol. Hepatol 15, 627-634.

Grimm, M.C. and Pavli, P. (2004) NOR Mutations and Crohn's Disease are Paneth Cells and their antimicrobial peptides the link? Gut 53, 1558-1560.

Kelly, P., Feakins, R., Domizio, P., Murphy, J., Bevins, C., Wilson, J., McPhail, G., Poulsom, R. and Dhaliwal, W. (2004) Paneth cell franule depletion in the human small intestine under infective and nutritional stress. Clin. Exp. Immunol 135, 303-309.

Bevins, C.L., Martin-Porter, E. and Ganz, T. (1999) Defensins and innate host defense of the gastrointestinal tract. Gut, 45, 911-915.

Oppenheim, J.J., Biragyn, A., Kwak, L.W. and Yang, D. (2003) Roles of antimicrobial peptides such as defensins in innate and adaptive immunity Ann. Rheum. Dis 62, 17-21.

Cunliffe, R.N. (2003) Defensins in the gastrointestinal tract. Mol. Immunol 40, 463-467.

Lehrer, R.I. and Ganz, T. (1999) Antimicrobial peptides in mamma- lian and insect host defence. Curr. Opin. Immunol. 11, 23-27.

Ganz, T. and Lehrer, R.I (1998) Antimicrobial peptides of verte- brates. Curr. Opin. Immunol. 10, 41-44.

Zasloff, M. (2002) Antimicrobial peptides of multicellular organ- isms. Nature, 415, 389-395.

Jones, D.E. and Bevins, C.L. (1992) Paneth cells of the human small intestine express an antimicrobial peptice gene. J. Biol. Chem. 267, 23216-23225.

Jones, D.E. and Bevins, C.L. (1993) Defensin-6 mRNA in human paneth cells: implications for antimicrobial peptides in host defense of the human bowel. FEBS Lett. 315, 187-192.

Daher, K.A., Selsted, M.E. and Lehrer, R.I. (1986) Direct inactivation of viruses by human franulocyte defensins. J. Virol. 60, 1068-1074.

Lichtenstein, A., Ganz, T., Selsted, M.E. and Lehrer, R.I. (1986) In vitro tumor cell cytolysis mediated by peptide defensins of human and rabbit granulocytes. Blood 68, 1407-1410.

Ganz, T. (2003) Nat. Immunology 3, 710-720.

Territo, M.C., Ganz, T., Selsted, M.E. and Lehrer, R.I. (1989) Monocyte-chemotactic activity of defensins from human neutrophils. J. Clin. Invest. 84, 2017-2020.

Yang, D., Chen, Q., Chertov, O. and Oppenheim, J.J. (2000) Human neutrophil defensins selectively chemo attract naïve T and immature dendritic cells. J. Leukoc. Biol. 68, 9-14.

Chertov, O., Michiel, D.F., Xu, L., Wang, J.M., Tani, K., Murphy, W.J., Longo, D.L., Taub, D.D. and Oppenheim, J.J. (1996) Identifi- cation of Defensin-1, Defensin-2 and CAP37/Azurocidin as T-cell Chemoattractant Proteins Released from Interleukin-8-stimulated neutrophils. J. Biol. Chem. 271, 2935-2940.

Yang, D., Chertov, O., Bykovskaia, S.N., Chen, Q., Buffo, M.J., Shogan, J., Anderson, M., Schroder, J.M., Wang, J.M., Howard, O.M. and Oppenheim, J.J. (1999)B-Defensins: Linking Innate and Adap- tive Immunity Through Dendritic and T Cell CCR6. Science 286, 525-528.

Yang, D., Chertov, O., and Oppenheim, J.J. (2001) Participation of mammalian defensins and cathelicidins in antimicrobial immunity: receptors and activities of human defensins and cathelicidin (LL-37) J. Leukoc. Biol. 69, 691-697.

Biragyn, A., Ruffini, P.A., Leifer C.A., Klyushnenkova, E., Shakhov, A., Chertov, O., Shirakawa, A.K., Farber, J.M., Segal, D.M., Oppenheim, J.J. and Kwak, L.W. (2002) Toll-like receptor 4-depen- dent activation of dendritic cells by B-defensin 2. Science 298, 1025- 1029.

Fernandez, E.J. and Lolis, E. (2002) Structure, function, and inhibi- tion of chemokines. Annu. Rev. Pharmacol. Toxicol. 42, 469-499.

Hugot, J.P., Chamaillard, M., Zouali, H., Lesage, S., Cezard, J.P., Belaiche, J., Almer, S., Tysk, C., O'Morain, C.A., Gassull, M., Binder, V., Finkel, Y., Cortot, A., Modigliani, R., Laurent-Puig, P., Gower-Rousseau, C., Macry, J., Colombel, J.F., Sahbatou, M. and Thomas, G. (2001) Association of NOD2 leucine-rich repeat variants with susceptibility to Crohn's disease. Nature 411, 599-603.

Ogura, Y., Bonen, D.K., Inohara, N., Nicolae, D.L., Chen, F.F., Ramos, R., Britton, H., Moran, T., Karaliuskas, R., Duerr, R.H., Achkar, J.P., Brant, S.R., Bayless, T.M., Kirschner, B.S., Hanauer, S.B., Nunez, G. and Cho, J.H. (2001) A frameshift mutation in NOD2 associated with susceptibility to Crohn's disease. Nature 411, 603- 606.

(56) References Cited

OTHER PUBLICATIONS

Ogura, Y., Inohara, N., Benito, A., Chen, F.F., Yanaoka, S. and Nunez, G. (2001) Nod2, a Nod1/Apaf-1 Family Member that is Restricted to Monocytes and Activates NV-kB. J. Biol. Chem. 276, 4812-4818.

Lala, S., Ogura, Y., Osborne, C., Hor, S.Y., Bromfield, A., Davies, S., Ogunbiyi, O., Nunez, G. and Flavell, R.A. (2003) Crohn's Disease and the NOD2 Gene: A Role for Paneth Cells. Gastroenterol. 125, 47-57.

Girardin, S.E., Boneca, I.G., Viala, J., Chamaillard, M., Labigne, A., Thomas, G., Philpott, D.J. and Sansonetti, P.J. (2003) Nod2 is a general sensor of peptideoglycan through nuramyl dipeptide (MDP) detection. J. Biol. Chem. 278, 8869-8872.

Inohara, N., Ogura, Y., Fontalba, A., Gutierrez, O., Pons, F., Crespo, J., Fukase, K., Inmura, S., Kusumoto, S., Hashimoto, M., Foster, S.J., Moran, A.P., Fernandez-Luna, J.L. and Nunez, G. (2003) Host recognition of bacterial muramyl dipeptide mediated through NOD2. J. Biol. Chem. 278, 5509-5512.

Inohara, N., Chamaillard, M., McDonald, C. and Nunez, G. (2004) NOD-LRR Proteins: Role in Host Microbial Interactions and Inflammatory Disease. Annu. Rev. Biochem. 74, 355-383.

Kobayashi, K.S., Chamaillard, M., Ogura, Y., Henegariu, O., Inohara, N., Nunez, G. and Flavell, R.A. (2005) Nod2-dependent Regulation of Innate and Adaptive Immunity in the Intestinal Tract. Science 307, 731-734.

Sampathkumar, P. and Gilchrist, M.L. (2004) Synthesis and characterization of bioconjugates of S-layer proteins. Bioconjugate Chem. 15, 685-693.

Avall-Jaaskelainen, S., Lindholm, A. and Palva, A. (2003) Surface display of the receptor-binding region of the *Lactobacillus brevis* S-layer protein in *Lactococcus lactis* provides nonadhesive lactococci with the ability to adhere to intestinal epithelial cells. Appl. Environ. Microbiol. 68, 5943-5951.

Sleytr, U.B. and Beveridge, T.J. (1999) Bacterial S-layers. Trends in Microbiol. 7, 253-260.

Antikainen, J., Anton, L., Sillanpää, J. and Korhonen, T.K. (2002) Domains in the S-layer protein CbsA of *Lactobacillus crispatus* involved in adherence to collagens, laminin and lipoteichoic acids and in self-assembly. Mol. Microbiol. 46, 381-394.

Lam, P.Y.S., Clark, C.G., Li, R., Pinto, D.J.P., Orwat, M.J., Galemmo, R.A., Fevig, J.M., Teleha, C.A., Alexander, R.S., Smallwood, A.M., Rossi, K.A., Wright, M.R., Bai, S.A., He, K., Luettgen, J.M., Wong, P.C., Knabb, R.M. and Wexler, R.R. (2003) Structure-based design of novel guanidine/benzamidine mimics: potent and orally bioavailable factor Xa inhibitors as novel anticoagulants. J. Exp. Med. 46, 4405-4418.

Rastall, R.A. and Maitin, V. (2002) Prebiotics and synbiotics towards the next generation. Curr. Opin. Biotechnol. 13, 490-498.

Fedorak, F.N. and Madsen, K.L. (2004) Probiotics and the management of inflammatory bowel disease. Inflamm. Bowel Dis. 10, 286-299.

Sartor, R.B. (2005) Probiotic therapy of intestinal inflammation and infections. Curr. Opin. Gastroenterol. 21, 44-50.

Dotan, I. and Rachmilevitz, D. (2005) Probiotics in inflammatory bowel disease: possible mechanisms of action. Curr. Opin. Gastroenterol. 21, 426-430.

Avall-Jaaskelainen, S. and Palva, A. (2005) *Lactobacillus* Surface layers and their applications. FEMS Microbiol. Rev. 29, 511-529.

Dorman, G. and Prestwich, G.D. (2000) Using photolabile ligands in drug discovery and development. Trends Biotechnol. 18, 64-77.

Bremer, A.A., Leeman, S.E. and Boyd, N.D. (2001) Direct evidence for the interactin of neurokinin A with the tachykinin NK receptor in tissue. J. Biol. Chem. 276, 22857-22861.

Chait, B.T. and Kent, S.B. (1992) Weighing naked proteins: practical, high-accuracy mass measurement of peptides and proteins. Science 257, 1885-1894.

Mann, M., Hendrickson, R.C. and Pandey, A. (2001) Analysis of proteins and proteomes by mass spectrometry. Annu. Rev. Biochem. 70, 437-473.

Grimm, M.C. and Pavli, P. (2004) NOD2 mutations and Crohn's disease: are Paneth cells and their antimicrobial peptides the link? Gut 53, 1558-1560.

Foster, N. and Hirst, B.H. (2005) Exploiting receptor biology for oral vaccination with biodegradable particles. Adv. Drug Del. Rev. 57, 431-450.

Sinha, V.R. and Trehan, A. (2005) Biodegradable microspeheres for protein delivery. J. of Contr. Rel. 90, 261-280.

Avall-Jaaskelainen, S, Lindholm, A. and Palva, A. (2003) Surface display of the receptor-binding region of the *Lactobacillus brevis* s-layer protein in *Lactococcus lactis* provises nonadhesive lactococci with the ability to adhere to intestinal epithelial cells. Appl. Env. Microbiol. 69, 2230-2236.

Sleytr, U.B. and Beveridge, T.J. (1999) Tr. In Microbiol. 7, 253-260.

Biragyn, A., Ruffini, P.A., Leifer C.A., Klyushnenkova, E., Shakhov, A., Chertov, O., Shirakawa, A.K., Farber, J.M., Segal, D.M., Oppenheim, J.J. and Kwak, L.W. (2002) Science 298, 1025-1029.

Chen, H., Xu, Z., Xu, N. and Cen, P. (2005) Efficient production of a soluble fusion protein containing human beta-defensin-2 in *E.coli* cell-free system. J. Biotechnol. 115, 307-315.

Xu, Z., Wang, F., Peng, L., Fang, X. and Cen, P. (2005) Expression of human B-Defensin-2 with multiple joined genes in *Eschenchia coli*. Appl. Biochem. Biotechnol. 120, 1-13.

Wu, Z., Ericksen, B., Tucker, K., Lubkowski, J. and Lu, W. (2004) Synthesis and characterization of human a-defensins 4-6. J Pept Res 64, 118-25.

Ericksen, B., Wu, Z., Lu, W. and Lehrer, R.I. (2005) Antibacterial activity and specificity of the six human a-defensins. Antimicrob Agents Chemother 49, 269-75.

Ouellette, A.J. (1999) Mucosal immunity and inflammation IV. Paneth cell antimicrobial peptides and biology of mucosal barrier. Am J Physiol 277, G257-61.

Ghosh, D. et al. (2002) Paneth cell trypsin is the processing enxyme for human defensin-5. Nat Immunol 3, 583-90.

Porter, E.M., Bevins, C.L., Ghosh, D. and Ganz, T. (2002) The multi-facted Paneth cell. Cell Mol Life Sci 59, 156-70.

Wehkamp, J. et al. "Reduced Paneth cell alpha-defensins in ileal Crohn's disease," PNAS Dec. 2005, 102(50):18129-18134.

Bauer et al. (2001) Structure determination of human and murine B-defensins reveals structural conservation n the absence of significant sequence similarity. Protein Science, 10:2470-2479.

Canadian Patent Office Action, corresponding to Canadian Patent Application No. 2,676,483, dated Nov. 21, 2011.

* cited by examiner

A

B

SEQUENCE LISTING

```
<160> NUMBER OF SEQ ID NOS: 3

<210> SEQ ID NO 1
<211> LENGTH: 94
<212> TYPE: PRT
<213> ORGANISM: Artificial Sequence
<220> FEATURE:
<223> OTHER INFORMATION: Synthetic construct

<400> SEQUENCE: 1

Met Arg Thr Ile Ala Ile Leu Ala Ala Ile Leu Leu Val Ala Leu Gln
1               5                   10                  15

Ala Gln Ala Glu Ser Leu Gln Glu Arg Ala Asp Glu Ala Thr Thr Gln
            20                  25                  30

Lys Gln Ser Gly Glu Asp Asn Gln Asp Leu Ala Ile Ser Phe Ala Gly
        35                  40                  45

Asn Gly Leu Ser Ala Leu Arg Thr Ser Gly Ser Gln Ala Arg Ala Thr
    50                  55                  60

Cys Tyr Cys Arg Thr Gly Arg Cys Ala Thr Arg Glu Ser Leu Ser Gly
65                  70                  75                  80

Val Cys Glu Ile Ser Gly Arg Leu Tyr Arg Leu Cys Cys Arg
                85                  90

<210> SEQ ID NO 2
<211> LENGTH: 68
<212> TYPE: PRT
<213> ORGANISM: Artificial Sequence
<220> FEATURE:
<223> OTHER INFORMATION: Synthetic Construct

<400> SEQUENCE: 2

Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 3
<211> LENGTH: 64
<212> TYPE: PRT
<213> ORGANISM: Artificial Sequence
<220> FEATURE:
<223> OTHER INFORMATION: Synthetic Construct
```

```
<400> SEQUENCE: 3

Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60
```

US 8,895,062 B2

SURFACE-LAYER PROTEIN COATED MICROSPHERES AND USES THEREOF

CROSS REFERENCE TO RELATED APPLICATIONS

This application claims priority from U.S. Provisional Patent Application No. 60/761,606, filed on Jan. 24, 2006; entitled "SURFACE-LAYER PROTEIN COATED MICROSPHERES," the contents of which are hereby incorporated by reference herein.

STATEMENT AS TO FEDERALLY SPONSORED RESEARCH

This invention was made with Government support under Grant Nos. AI056264 and AI061482. The Government has certain rights in the invention.

GOVERNMENT LICENSE RIGHTS

This invention was made with government support under AI056264 and AI061482 awarded by the National Institute of Health. The government has certain rights in the invention.

BACKGROUND OF THE INVENTION

1. Field of the Invention

The invention relates to microspheres and delivery of therapeutic agents, and more specifically, to microspheres coated with surface-layer proteins having affinity for certain tissues for delivery of a therapeutic agent, such as, delivery of defensins, particularly HD5α in the treatment of inflammatory conditions of the bowel, such as Crohn's disease and/or ulcerative colitis.

2. Description of the Related Art

The surface properties and surface structures of bacteria are important in regulating bacterial adhesion to host cells [1]. Adherence to constituents of the extracellular matrix, such as glycoproteins like fibronectin and laminin as well as to different types of collagen, has been shown to be mediated through surface layer proteins in various bacterial species [2, 3]. These adhesive properties have been linked to the ability of bacteria to express virulence [4-7] as well as probiotic properties [8, 9].

In the case of Lactobacilli, various studies have shown the importance of the surface-layer or S-layer protein in adhesion of the bacterium to the intestinal epithelium [9-11]. S-layers are one of the most common surface structures of many archaebacteria and eubacteria. A shared feature of S-layers is the ability to self-assemble and form a regularly ordered, planar array of proteinaceous subunits [12]. Various functions have been assigned to S-layers. Most species of lactobacilli contain two or more genes encoding S-layer proteins. Three slp genes (slpB, slpC and slpD) have been identified in *L. brevis* ATCC 14869 whereas only a single gene slpA has been identified *L. brevis* ATCC 8287. Because S-layer lattices show identical pore size and morphology, they act as precise molecular sieves for the cell. They act as a protective shield against exceptionally high ion concentrations as well as certain bacterial parasites [13]. The SlpA surface protein of *Lactobacillus brevis* is reported to be essential for adhesion of this bacterium to intestinal cells through its interaction with the extracellular matrix component fibronectin [11].

Microbial infection and inflammation is a constant risk in the mucosal surface of the gastrointestinal tract, which comprises the first line of defense against a variety of microorganisms. Remarkably, this mucosal immune system has the ability to distinguish pathogens from the commensal microflora and to elicit the appropriate immune response [14-16]. The intestinal mucosa is covered by a single layer of epithelial cells; separating mucosa associated lymphoid tissue from surface antigens. The epithelium provides both a barrier as well as a signaling function against infection [17]. The epithelial cells as well as immune cells of the subepithelial compartment, including lymphocytes, monocytes, macrophages, polymorphonuclear leukocytes and dendritic cells, induce the host innate and adaptive immune systems. Activation of the innate host defense by microbes occurs via the specific recognition of microbial molecules, known as pathogen-associated molecular patterns or PAMPs [18].

Host cells detect these patterns through receptors, including members of the Toll-like receptor family and the nucleotide-binding site/leucine rich repeat proteins such as NOD1 and NOD2 [19-21]. Toll-like receptors are type I integral membrane glycoproteins belonging to the superfamily of interleukin-1 receptors. They play an essential role in the initiation of the innate antimicrobial immune response in plants, insects and mammals [22]. The extracellular part of the receptors contains copies of a motif known as leucine-rich repeat, thought to be directly involved in the recognition of microbial components. In humans, ten Toll-like receptors can be found, designated TLR1-TLR10, each recognizing conserved microbial molecules [23-27]. Toll-like receptors are localized on the cell surface or in endosome-lysosome intracellular compartments of immune cells [28,29]. Most of the current studies on the biological role and distribution of Toll-like receptors have focused on dendritic cells and macrophages. In contrast, the expression patterns and role of TLR's in antigen presenting cells present in the mucosal surface as well as epithelial cells has been poorly described.

Crohn's disease is a chronic disease of the intestine characterized by inflammation of the gut. The disease can be located from the oral cavity to the rectum although in almost 70% of patients the distal ileum is affected. Crohn's disease and ulcerative colitis constitute the two major chronic inflammatory bowel diseases (IBD's), affecting one in 500 individuals [30]. The etiopathogenesis of Crohn's disease has been linked recently to a diminished expression of intestinal antimicrobial peptides called defensins [31-36].

Defensins are cationic and cysteine-rich peptides with molecular weights of 3 to 5 kDa. Based on the connectivity of the six cysteine residues, human defensins are classified into α and β subfamilies [37-39]. The α-defensins are predominantly expressed in neutrophils (human neutrophil peptide 1-4) or specialized cells of the intestinal epithelium called Paneth cells (human defensin 5 and 6α) [40,41]. Human β-defensins are found predominantly in various epithelial cells and tissues. Defensins play an important role in the host innate immune defense, not only showing antibiotic and antifungal activity but also kill certain enveloped viruses and act selectively cytotoxic to tumor cells [42,43]. Importantly, human α and β-defensin also act as immune modulators in adaptive immunity [44].

Initial studies showed that α-defensins chemoattract monocytes [45]. Subsequently, α-defensins were reported to chemoattract different subsets of T lymphocytes and immature dendritic cells [46,47]. More recently, similar functions have been reported for β-defensins [48-50]. These studies showed that β-defensins selectively chemoattract memory T cells and immature dendritic cells. In addition, it was shown that human β-defensin 2 act directly as endogenous ligands for Toll-like receptors, mediating signaling for dendritic cell maturation in vivo. Defensins and chemokines share a striking structural resemblance, adopting a disulfide stabilized core structure of three anti-parallel β-sheets [51].

The recent discovery of several genetic loci showing a significant association with Crohn's disease has greatly enhanced the understanding of underlying pathogenic mechanisms. In particular, NOD2 has been identified as the first gene firmly associated with Crohn's disease susceptibility [52,53]. NOD2 is a cytoplasmic protein that senses components of the microbial cell wall and regulates inflammatory processes and apoptosis. The protein is composed of two N-terminal caspase recruitment domains, a nucleotide binding and oligomerization domain and contains ten leucine-rich repeats at its C-terminus. It is expressed constitutively in particular in macrophages, neutrophils and dendritic cells [54] as well as Paneth cells in the small intestine [55]. NOD2 specifically recognizes muramyl dipeptide, a peptidoglycan motif present in the cell wall of both gram-negative and gram-positive bacteria [56]. After recognition, NOD2 has been shown to activate signaling pathways involved in inflammation in vitro through NF-κB activation [57,58]. In addition, NOD2 activation has been linked to innate immunity [59]. In NOD2 knockout mice, expression of α-defensins was markedly decreased suggesting that NOD2 plays a role in intestinal host defense. This provides further evidence to the notion that defensins and their relation to Toll-like receptors may play a key role in maintaining immune homeostasis.

Importantly, human α and β-defensin also act as immune modulators in adaptive immunity [44]. Further, the etiopathogenesis of Crohn's disease has been linked recently to a diminished expression of the anti-microbial peptides defensins [31-36]. Thus, it would be advantageous to provide a method for delivery of defensins to intestinal tissue to provide an increase of this intestinal anti-microbial peptide defensins.

SUMMARY OF THE INVENTION

The present invention relates to a delivery of a therapeutic agent to specific tissues within a mammalian biological system by including s-layer proteins of a microbial agent having affinity for such specific tissue.

In one aspect, the present invention relates to a delivery device for administering a therapeutic agent to specific tissue, the method comprising:
encapsulating a therapeutic agent into a microsphere; and
coating at least a section of the microsphere with a bacterial S-layer protein having affinity for the specific tissue.

In another aspect, the present invention relates to a delivery device for delivery of a therapeutic agent to specific tissue, the device comprising a therapeutic agent encapsulated within a microsphere, wherein the microsphere is coated on the surface with S-layer proteins from Lactobacilli for adhesion to the intestinal epithelium.

In yet another aspect, the present invention relates to a delivery device for delivery of a therapeutic agent for treatment of Crohn's disease, the delivery device comprising a microsphere encapsulating defensin, wherein the microsphere is coated on the surface with *Lactobacillus brevis* SlpA surface layer protein.

In a further aspect, the present invention relates to a method of increasing anti-microbial peptides at intestinal epithelium, the method comprising:
providing an anti-microbial peptide encapsulated within a microsphere, wherein the microsphere has at least a section of the surface of coated with a bacterial S-layer protein having affinity for the intestinal epithelium.

Preferably, the S-layer proteins are from Lactobacilli having adhesion molecules for adhering to the intestinal epithelium.

Other aspects and advantages of the invention will be more fully apparent from the ensuing disclosure and appended claims.

DETAILED DESCRIPTION OF THE INVENTION

Definitions

Figure 1:
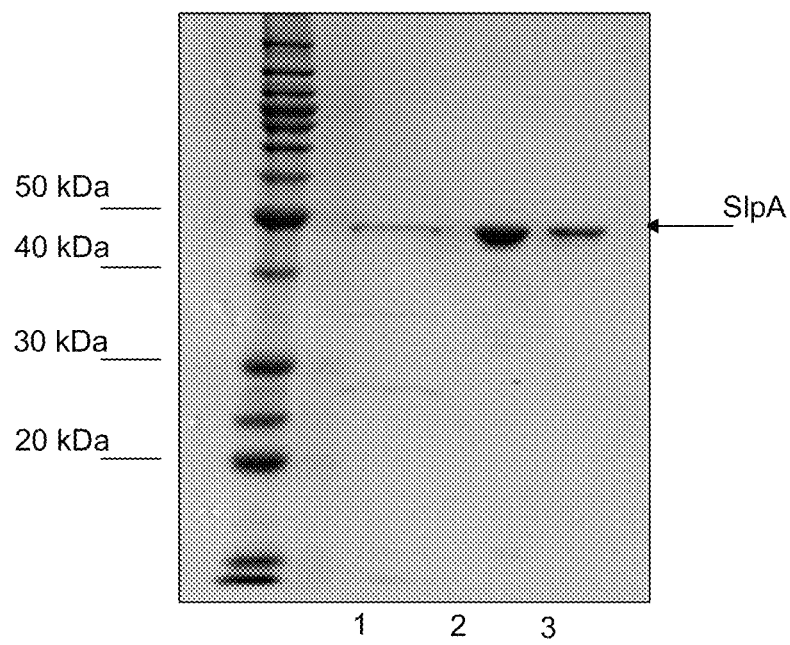
FIG. 1 shows the purification of *Lactobacillus brevis* SlpA surface layer protein. The SlpA protein was purified by gel permeation chromatography after extraction of the cells with 5M LiCl (lane 1) on a Sephacryl S100 column (lane 2). After purification, protein was dialyzed and concentrated (lane 3). Samples were analyzed by SDS-PAGE and proteins are visualized by EZblue staining (Pierce).

"Analog" means a peptide having a sequence which is modified based on a native peptide and which retains some or all of the activity of the native compound or exhibits enhanced activity relative to the native compound, or a sequence which is cleaved in vivo to yield a peptide having such activity. For example, a sequence-modified defensin that retains native defensin activity is an analog. Similarly, a sequence-modified surface layer protein that retains the capacity to self-associate and/or affinity for extracellular matrix components is an analog. Analogs may have, for example, one or more insertions, deletions, truncations, extensions, substitutions, or combinations of the foregoing.

"Deletion" means deletion of one or more native amino acid residues from between native amino acid residues.

"Truncation" means deletion of one or more native amino acid residues from an N-terminus or C-terminus of a native sequence.

"Extension" means addition of one or more native amino acid residues at an N-terminus or C-terminus of a native sequence.

"Substitution" means replacement of one or more amino acid residues within a native sequence (e.g., a native defensin or a native surface layer protein) with another amino acid.

"Insertion" means insertion of one or more amino acid residues between two native residues of a native sequence (e.g., a native defensin or a native surface layer protein). In some cases, the substituted or inserted amino acid acts as a functional equivalent or results in a silent alteration. Conservative substitutions may, for example, be selected from other members of the class to which the substituted amino acid belongs. Examples of nonpolar (hydrophobic) amino acids include alanine, leucine, isoleucine, valine, proline, phenylalanine, tryptophan and methionine. Examples of polar neutral amino acids include glycine, serine, threonine, cysteine, tyrosine, asparagine, and glutamine. Examples of positively charged (basic) amino acids include arginine, lysine and histidine. Examples of negatively charged (acidic) amino acids include aspartic acid and glutamic acid. Branched, looped, and branched/looped sequences are also analogs.

"Defensin" means native defensin peptides, propeptides and prepropeptides, and analogs of such defensin peptides, propeptides and prepropeptides. For example, the term "defensin" includes α-defensins, such as HD5α, and β-defensins, such as HBD1 and HBD2, as well as analogs of such α- and β-defensins.

"HBD1" means human β-defensin 1.

"HBD2" means human β-defensin 2.

"HD5α" means human α-defensin 5.

"Peptide" and "protein" are used interchangeably to refer to amino acid sequences of any length.

"Surface layer protein" means self-assembling proteins, such as *Lactobacillus brevis* surface-layer protein SlpA, that are involved in bacterial-host adhesion via specific interactions with components of the extracellular matrix, such as fibronectin, laminin, fibrinogen and collagen, as well as analogs of surface layer proteins.

The invention provides surface-layer protein coated microspheres for delivery of a therapeutic agent to the intestine. These surface-layer protein coated microspheres generally include a core encapsulated by a microsphere which is coated by surface layer protein. The core includes a therapeutic agent, such as a defensin.

The invention also includes methods of making and using the surface-layer protein coated microspheres of the invention for administering therapeutic agents to a subject in need thereof.

The invention also includes pharmaceutical dosage units that include the surface-layer protein coated microspheres of the invention.

The invention further includes various labeled defensins, useful, for example, in diagnostic applications or in the study of the properties and actions of defensins.

The invention further includes the use of defensins, particularly HD5α in the treatment of inflammatory conditions of the bowel, such as Crohn's disease and/or ulcerative colitis.

Section headings are included to facilitate the reader and are not intended to limit the scope of the invention in any way.

Core and Therapeutic Agent

The invention includes a core with a therapeutic agent. The core is typically produced by admixing the therapeutic agent with inter alia, a pharmaceutically acceptable carrier. However, the core may in some instances be a pure or substantially pure therapeutic agent, such as a pure or substantially pure defensin.

Therapeutic Agent

The core includes a therapeutic agent. In a composition for administration to humans, the therapeutic agent must be sufficiently pure for administration to humans—the therapeutic agent must be supplied to the composition at a pharmaceutically acceptable level of purity. At a basic level, this means that the risk of side effects from any impurities does not outweigh the beneficial effects provided by the therapeutic agent. Preferably the therapeutic agent is at least 95, 96, 97, 98, 99, 99.5, or 99.9 percent pure.

The core may include 1, 2, 3, 4, 5 or more therapeutic agents. For example, the core may include a single defensin peptide, such as HBD1, HBD2, HD5α, or an analog thereof. Alternatively, the core may include two or more therapeutic agents, such as two or more defensins, e.g., selected from HBD1, HBD2, HD5α, or analogs thereof. Further, the core may include a defensin with a non-defensin peptide, such as a steroid (e.g., budesonide), an antibiotic, an anti-inflammatory, and/or an immune modulator. And, in an alternative aspect of the invention, the core may include one or more non-defensin peptides, such as one or more steroids (e.g., budesonide), antibiotics, anti-inflammatories, and/or immune modulators.

Defensins

The preferred therapeutic agent is a defensin peptide, which is properly folded and exhibits activity comparable to the native activities of defensins. Suitable defensins for use in the present invention include, without limitation, α-defensins, such as HD5α, and β-defensins, such as HBD1 and HBD2, as well as analogs of such α- and β-defensins. In some embodiments the core is pure or substantially pure defensin peptide, such as HBD1, HBD2, HD5α, or an analog thereof. For example, the therapeutic agent may include:

HD5α peptide: Met-Arg-Thr-Ile-Ala-Ile-Leu-Ala-Ala-Ile-Leu-Leu-Val-Ala-Leu-Gln-Ala-Gln-Ala-Glu-Ser-Leu-Gln-Glu-Arg-Ala-Asp-Glu-Ala-Thr-Thr-Gln-Lys-Gln-Ser-Gly-Glu-Asp-Asn-Gln-Asp-Leu-Ala-Ile-Ser-Phe-Ala-Gly-Asn-Gly-Leu-Ser-Ala-Leu-Arg-Thr-Ser-Gly-Ser-Gln-Ala-Arg-Ala-Thr-Cys-Tyr-Cys-Arg-Thr-Gly-Arg-Cys-Ala-Thr-Arg-Glu-Ser-Leu-Ser-Gly-Val-Cys-Glu-Ile-Ser-Gly-Arg-Leu-Tyr-Arg-Leu-Cys-Cys-Arg (SEQ ID NO: 1) or an amino acid sequence having at least 90% homology to SEQ ID NO: 1 and exhibits activity comparable to the native activities of defensins.

HBD1 peptide: Met-Arg-Thr-Ser-Tyr-Leu-Leu-Leu-Phe-Thr-Leu-Cys-Leu-Leu-Leu-Ser-Glu-Met-Ala-Ser-Gly-Gly-Asn-Phe-Leu-Thr-Gly-Leu-Gly-His-Arg-Ser-Asp-His-Tyr-Asn-Cys-Val-Ser-Ser-Gly-Gly-Gln-Cys-Leu-Tyr-Ser-Ala-Cys-Pro-Ile-Phe-Thr-Lys-Ile-Gln-Gly-Thr-Cys-Tyr-Arg-Gly-Lys-Ala-Lys-Cys-Cys-Lys (SEQ ID NO: 2) or an amino acid sequence having at least 90% homology to SEQ ID NO: 2 and exhibits activity comparable to the native activities of defensins.

HBD2 peptide: Met-Arg-Val-Leu-Tyr-Leu-Leu-Phe-Ser-Phe-Leu-Phe-Ile-Phe-Leu-Met-Pro-Leu-Pro-Gly-Val-Phe-Gly-Gly-Ile-Gly-Asp-Pro-Val-Thr-Cys-Leu-Lys-Ser-Gly-Ala-Ile-Cys-His-Pro-Val-Phe-Cys-Pro-Arg-Arg-Tyr-Lys-Gln-Ile-Gly-Thr-Cys-Gly-Leu-Pro-Gly-Thr-Lys-Cys-Cys-Lys-Lys-Pro (SEQ ID NO: 3) or an amino acid sequence having at least 90% homology to SEQ ID NO: 3 and exhibits activity comparable to the native activities of defensins.

The defensin may be an analog of a native defensin peptide, e.g., an analog of HBD1, HBD2, or HD5α. For example, the defensin may be an analog of a native defensin peptide having insertions, deletions, truncations, extensions, substitutions, or combinations of the foregoing, relative to the native sequence, but retaining some or all of the activity of the native compound or having enhanced activity relative to the native compound. For example, the defensin peptide may be an analog, having 1, 2, 3, 4, 5, 6, 7, 8, 9, 10 or more amino acid residues omitted from the N-terminus and/or C-terminus. The defensin peptide may be an analog, having 1, 2, 3, 4, 5, 6, 7, 8, 9, 10 or more amino acid residues deleted from within the amino acid sequence. The defensin peptide may be an analog, having 1, 2, 3, 4, 5, 6, 7, 8, 9, 10 or more amino acid residues inserted from within the amino acid sequence. The defensin peptide may be an analog, having 1, 2, 3, 4, 5, 6, 7, 8, 9, 10 or more amino acid residues added at the N-terminus or C-terminus thereof. The defensin peptide may be an analog, having 1, 2, 3, 4, 5, 6, 7, 8, 9, 10 or more amino acid substitutions within the amino acid sequence. The defensin peptide may be an analog having a combination of 1, 2, 3, 4, 5, 6, 7, 8, 9, 10 or more amino acid insertions, deletions, truncations, extensions, and/or substitutions in the amino acid sequence. The defensin peptide may also be provided as a component of a fusion protein, in which the defensin is fused to a heterogeneous protein or peptide. The therapeutic agent may also be a derivative of a defensin, such as a defensin coupled to a polyethylene glycol moiety or acetylated to a fatty acid moiety.

Carriers and Other Excipients in the Core

Where the core includes a carrier with the therapeutic agent, the carrier must be acceptable in the sense of being compatible with any other ingredients in the pharmaceutical composition and should not be unduly deleterious to the subject in that the benefits provided by the carrier are outweighed by the detriments. In one embodiment, the core includes buffer salts and/or protein stabilizers.

Microspheres

The core is enclosed in a pharmaceutically acceptable microsphere. The manufacture and use of microspheres is well established [81]. Microspheres suitable for use in the invention may be biodegradable or non-biodegradable; however, biodegradable coatings are preferred.

The coating of the microsphere may be any suitable polymeric substance. Commonly used polymers include polyorthoesters, polyanhydrides, polyamides, polyalkylcyanoacrylates, polyesters (e.g., lactides/glycolides or polycaprolactones), polyphosphazines, pseudo-polyamino acids, proteins (e.g., albumin, globulin, gelatin, collagen or casein), and polysaccharides (e.g., starch, cellulose, chitosan, dextran, or alginic acid) [81].

A variety of techniques for manufacturing microspheres is available [81]. Examples of suitable techniques include spray drying, multiple emulsion, phase separation, dispersion/solvent extraction/evaporation, solid encapsulation/single emulsion/solvent extraction, nonaqueous o/o emulsion methods. The entire disclosure of Sinha & Trehan [81], and the references cited therein, is incorporated herein for their teaching concerning the manufacture of microspheres.

Surface Layer Protein Coating

The microspheres are coated with a surface layer protein. The surface layer proteins may be any of a wide variety of self-assembling proteins that are involved in bacterial-host adhesion via specific interactions with components of the extracellular matrix. For example, a preferred set of surface layer proteins are those which interact with fibronectin, laminin, fibrinogen and/or collagen. Such interaction can be assessed, for example, using surface plasmon resonance. Preferred surface layer proteins are those which interact with high affinity with an extracellular matrix component, such as fibronectin, laminin, fibrinogen and/or collagen. For example, in one embodiment, the surface layer protein has an affinity for fibronectin, laminin, fibrinogen and/or collagen measured using surface plasmon resonance which is greater than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 nM. In a related embodiment, preferred surface layer proteins are those which interact with polymorphonuclear leukocytes.

The surface layer protein may, for example, be a surface layer protein from *Lactobacillus acidophilus*, *Lactobacillus helveticus*, *Lactobacillus crispatus*, *Lactobacillus amylovorus*, *Lactobacillus gallinarum*, *Lactobacillus kefir*, *Lactobacillus parakefir*, *Lactobacillus gasseri*, or *Lactobacillus johnsonii*. In one embodiment, the surface layer protein is SlpA, SlpB, SlpD, CbsB, or SlpnB from *Lactobacillus brevis*; CbsA protein of *Lactobacillus crispatus*, a *Bacillus cereus* surface layer protein, or an analog any of the foregoing.

In another embodiment, the surface layer protein is a protein including an extracellular matrix component binding region from a native surface layer protein. Other examples of suitable surface layer proteins are those produced by the organisms set forth in Table 1, and analogs thereof:

TABLE 1

S-layer proteins whose amino acid sequences are known

| Species | Strain | Gene | GenBank accession no. |
|---|---|---|---|
| *Aeromonas hydrophila* | TF7 | ahs | L37348 |
| *Aeromonas salmonicida* | A450 | vapA | M64655 |
| *Bacillus anthracis* | Sterne derivative substrain 9131 | sap | Z36946 |
| | | eag | X99724 |
| *Brevibacillus brevis (Bacillus brevis)* | 47 | owp | M14238 |
| | | mwp | M19115 |
| *Brevibacillus brevis (Bacillus brevis)* | HPD31 | HWP | D90050 |
| *Bacillus licheniformis* | HM105 | olpA | U38842 |
| *Bacillus sphaericus* | P1 | sequence 8 | A45814 |
| *Bacillus sphaericus* | 2362 | gene 125 | M28361 |
| | | gene 80 | |
| *Bacillus stearothermophilus* | PV72/p6 | sbsA | X71092 |
| | PV72/p2 | sbsB | X98095 |
| *Bacillus stearothermophilus* | ATCC 12980 | sbsC | AF055578 |
| *Bacillus thuringiensis* | | ctc | AJ012290 |
| *Campylobacter fetus* subsp. *fetus* | | sapA | J05577 |
| *Campylobacter fetus* subsp. *fetus* | 23B | sapA1 | L15800 |
| *Campylobacter fetus* subsp. *fetus* | 82-40LP3 | sapA2 | S76860 |
| *Campylobacter fetus* subsp. *fetus* | 84-91 | sapB | U25133 |
| | CIP 5396T | sapB2 | AF048699 |
| *Campylobacter rectus* | 314 | crs | AF010143 |
| *Caulobacter crescentus* | CB15 | rsaA | M84760 |
| *Clostridium thermocellum* | NCIMB 10682 | slpA | U79117 |
| *Corynebacterium glutamicum* | ATCC 17965 | csp2 | X69103 |
| *Deinococcus radiodurans* | | HPI gene | M17895 |
| *Halobacterium halobium* | | csg | J02767 |
| *Haloferax volcanii* | | | M62816 |
| *Lactobacillus acidophilus* | ATCC 4356 | slpA | X89375 |
| | | slpB | X89376 |
| *Lactobacillus brevis* | ATCC 8287 | | Z14250 |
| *Lactobacillus crispatus* | JCM 5810 | cbsA | AF001313 |
| *Lactobacillus helveticus* | CNRZ 892 | slpH1 | X91199 |
| *Lactobacillus helveticus* | CNRZ 1269 | slpH2 | X92752 |
| *Methanococcus voltae* | | sla | M59200 |
| *Methanosarcina mazei* | S-6 | slgB | X77929 |
| *Methanothermus fervidus* | DSM 2088 | slgA | X58297 |
| *Methanothermus sociabilis* | DSM 3496 | slgA | X58296 |
| *Rickettsia prowazekii* | Brein 1 | spaP | M37647 |
| *Rickettsia rickettsii* | R | p120 | X16353 |
| *Rickettsia typhii* | Wilmington | slpT | L04661 |
| *Serratia marcescens* | Isolate 8000 | slaA | AB007125 |
| *Staphylothermus marinus* | F1 | | US7967 |
| *Thermoanaerobacter kivui* (*Acetogenium kivui*) | DSM 2030 | slp | M31069 |
| *Thermus thermophilus* | HB8 | slpA | X57333 |

*This table was adapted from a table included in Sára et al., reference [89].

The surface-layer protein coated microspheres preferably have an average particle size ranging from about 30 Å to about 2000 µm. In a related embodiment, small microspheres are preferred, wherein the average particle size ranges from about 30 Å to about 200 nm.

In another embodiment, large microspheres are preferred, wherein the average particle size ranges from about 15 um to about 50 µm, preferably about 15 to about 35 µm, more preferably about 15 to about 25 µm. In the foregoing compositions, preferably about 90% of the microspheres in the composition are within the ranges indicated, more preferably about 95, 96, 97, 98, 99, or 99.9% of the microspheres in the composition are within the ranges indicated.

The surface layer proteins are preferably layered on the microsphere substrate as a monomolecular crystalline array that covers the microsphere in an amount that causes adhesion but not in an amount that prevents the degradation of the biodegradable microsphere polymeric material because the degradation is necessary to allow the release of the defensin.

Pharmaceutical Compositions and Dosage Units

The invention provides pharmaceutical dosage units that include the surface-layer protein coated microspheres of the invention. Such pharmaceutical dosage units generally include the surface-layer protein coated microspheres of the invention formulated with a carrier. However, it will be appreciated that a carrier is not always necessary. The carrier may be a solid or a liquid, or both, and is preferably formulated with surface-layer protein coated microspheres as a unit-dose composition, for example, a tablet including the surface-layer protein coated microspheres. The composition may be prepared by any of the well-known techniques of pharmacy including, but not limited to, admixing the components, optionally including one or more accessory ingredients. The therapeutic agents are provided in an amount effective to achieve the desired pharmacological effect, as described above, and in a quantity appropriate to achieve 1, 2, 3, 4 or 5 daily doses.

In certain embodiments, the compositions of the invention are designed to deliver the therapeutic agents to the site of disease. For example, where the condition is Crohn's disease, an oral composition can be formulated to deliver the therapeutic agent(s) to ulcerated or inflamed tissue in the large intestine and/or the colon, releasing the therapeutic agent(s)

along the length of the small intestine and the colon, and/or along the distal portion of the small intestine and in the colon. Similarly, where the disease condition is ulcerative colitis, an oral composition can be formulated to release the therapeutic agent(s) along the length of the distal portion of the small intestine and in the colon, or along the length of the colon. Moreover, where the disease site is in the colon (e.g., ulcerative colitis), the therapeutic agent(s) can be formulated as a suppository or an enema.

Other suitable compositions include, for example, oral compositions such as mouth washes for treatment of inflammatory conditions of the oral cavity or throat; vaginal compositions for treatment of inflammatory conditions of the vaginal cavity or opening; intra-uterine compositions for inflammatory conditions of the uterus; eye compositions, such as salves for treatment of inflammatory conditions of the eye or conjunctiva; as well as topical compositions for dermal application to treat inflammatory conditions of the skin. The foregoing compositions preferably include surface-layer protein coated microspheres according to the invention.

Compositions of the present invention suitable for oral administration can be presented as discrete dosage units such as capsules, cachets, tablets, or lozenges, each containing a predetermined amount of one or more therapeutic agents. The surface-layer protein coated microsphere component of the composition can, for example, take the form of a powder or granules. Solids, such as tablets or pellets, including the surface-layer protein coated microspheres can themselves be coated, e.g., enterically coated. The compositions can be provided having microparticles of the invention suspended, e.g., in an aqueous liquor or a non-aqueous liquid, such as a syrup, an elixir, an emulsion, or a draught.

Oral compositions for treatment of intestinal conditions are preferably solid dosage forms and can include any of a wide variety of components known to assist therapeutic agents to pass through the stomach and be released in the intestine, such as in the proximal small intestine, distal small intestine, and/or in the colon. For example, the surface-layer protein coated microspheres of the invention may be provided as components of a tablet or capsule, which may in turn be coated (e.g., enterically coated).

Preferred coatings for tablets or capsules comprising surface-layer protein coated microspheres of the invention for oral administration to effect delivery of the surface-layer protein coated microspheres to a disease site in the small intestine or colon include one or more AZO-bonded coatings, enteric coatings, pH sensitive coatings, coatings that dissolve in a pH range of about 5.5 to about 7, methacrylic polymers, time release coatings, microcapsules, biodegradable coatings, and redox sensitive coatings.

Treatment Methods

The surface-layer protein coated microspheres and pharmaceutical compositions of the invention are useful for treating disorders affecting the digestive system or mucosal tissues, such as conditions involving infection or inflammation of the digestive system or mucosal tissues. Examples of conditions suitably treated using the methods and compositions of the invention include inflammatory conditions of the intestine, such as celiac disease, bacterial overgrowth, yeast imbalance, peptic ulcer disease, and fissures of the intestine, travelers' diarrhea, pouchitis, inflammatory bowel disease ("IBD," e.g., ulcerative colitis and Crohn's disease), and various forms of colitis, such as diversion colitis, non-specific colitis, ulcerative colitis, infectious colitis (e.g., pseudomembranous colitis such as *Clostridium difficile* colitis, *salmonella* enteritis, *shigella* infections, yersiniosis, cryptosporidiosis, microsporidial infections, and viral infections). The methods and compositions of the invention are also useful in the treatment of irritable bowel syndrome.

According to other embodiments of the present invention, methods of treating a subject in need of such treatment include administering an effective amount of a composition of this invention to the subject and/or delivering an effective amount of a composition of this invention to the digestive system and/or mucosal tissues of a subject. Administration is preferably by the oral route, preferably by ingestion. The effective amount will vary somewhat from composition to composition, and subject to subject, and will depend upon factors such as the age, species, gender and/or condition of the subject and the route and mode of delivery. Such dosages can be determined in accordance with routine pharmacological procedures known to those skilled in the art. The frequency of administration can be 1, 2, 3, 4, 5, or more times per day/week/month/year or as necessary to treat the condition. The duration of treatment depends on the type of condition being treated and can be for as long as the life of the patient.

Subjects suitable to be treated according to the present invention include, but are not limited to, avian and mammalian subjects, and are preferably mammalian. Mammals treatable according to the present invention include, but are not limited to, canines, felines, bovines, caprines, equines, ovines, porcines, rodents (e.g., rats and mice), lagomorphs, primates, humans, and the like, and mammals in utero. Any mammalian subject in need of being treated according to the present invention is suitable. Human subjects are preferred. Human subjects of both genders and at any stage of development can be treated according to the present invention.

The method generally involves the administration of surface-layer protein coated microspheres including a therapeutic agent in a pharmaceutically effective amount. The composition may be administered alone or in combination with other compositions. The composition may include 1, 2, 3, 4, 5 or more therapeutic agents.

In a preferred embodiment, the composition of the invention is administered to a subject having a disorder involving inflammation of the digestive system and/or mucosal tissues. In certain embodiments, the disorder is a bowel condition, and the composition releases the therapeutic agent(s) in the lumen of the bowel. Preferably the surface layer protein interacts or binds with extracellular membrane components, such as fibronectin or laminin, in a manner which prolongs its traversal through the gut and thereby prolongs exposure of a disease site, such as inflamed or ulcerated tissue, with the therapeutic agent.

The defensin peptide can be administered via the composition of the invention as a monotherapy. Alternatively, the defensin peptide can be administered as a component of a combination therapy regimen employing at least one defensin peptide and one or more other compounds. Where a combination therapy is used, the various therapeutic compounds can be administered separately or together as components of a single composition. Examples of compounds suitably administered with a defensin peptide for treatment of an inflammatory or infectious bowel condition include local steroids (e.g., budesonide), antibiotics, anti-inflammatories, and immune modulators.

Depending on the specific condition or disease state to be treated, subjects are administered compounds of the present invention at any suitable therapeutically effective and safe dosage, as can readily be determined within the skill of the art and without undue experimentation in light of the present disclosure.

The defensin peptides, and other compounds used in the compositions and methods of the invention can be administered or delivered per se as well as in the form of pharmaceutically acceptable esters, salts, and other physiologically functional derivatives thereof and/or in a pharmaceutically acceptable carrier.

Labeled Defensins

The invention also includes defensins which incorporate a cross-linking and/or an affinity moiety. Such modified defensins are useful, for example, for the study of the interactions between defensins and receptors, such as chemokine receptors. Further, the invention includes defensins which incorporate a fluorescent moiety. Such defensins are useful, for example, in the study interactions with the cellular components. The invention also includes kits comprising the foregoing modified defensins, along with reagents and instructions for using the modified defensins to study interactions between defensins and receptors and/or interactions between defensins and the cellular components. Preferred labeled defensins are HBD1, HBD2, and HD5α.

Examples

Studies Involving Surface Layer Protein A

The following examples illustrate embodiments of the invention and are not intended to limit the scope of the invention.

Materials

*Lactobacillus brevis* ATCC 8287 was obtained from the American Type Culture Collection (Manassas, Va.). Fibronectin (human plasma), Laminin (basement membrane of Engelbreth-Holm-Swarm mouse sarcoma) and Collagen (human placenta Type IV) were obtained from Sigma. Fibrinogen (human plasma) was obtained from Calbiochem. Chemicals were purchased from Sigma. Protein concentration was determined by BCA assay (Biorad).

SlpA Purification

The SlpA protein was purified essentially as described previously [60]. In short, *L. brevis* ATCC 8287 was grown unstirred in MRS Broth (Difco) at 37° C. for 3 days after inoculation with 2% (v/v) of a 2 day culture. Cells were harvested by centrifugation at 14,000×g for 20 min at 4° C. The cell pellets were resuspended and washed twice in distilled water to remove remaining broth. To extract the SlpA protein, the cell pellet was resuspended in 5M LiCl and incubated on ice for 30 min. The extract was subjected to centrifugation at 14,000×g for 20 min at 4° C. The resulting supernatant was further purified using a Sephacryl S100 HiPrep 26/60 (Pharmacia) gel filtration column equilibrated in 5M LiCl. Protein was eluted at 0.5 ml/min and collected fractions (1.5 ml) containing the purified SlpA protein were analyzed by 12% SDS-PAGE (Novex) and visualized by EZblue staining (Pierce). Protein was concentrated using Centriprep centrifugal filter devices (Millipore) with a 30 kDa molecular weight cutoff.

Negative Stain Electron Microscopy

S-layers on whole *L. brevis* cells as well as purified monomeric/oligomeric SlpA (0.5 mg/ml in ddH$_2$O) protein were visualized by negative staining using 1% neutralized phospho tungstic acid solution for 10 sec. on carbon coated, glow-discharged copper mesh (400) grids pretreated with vinylec. Samples were analyzed on a Zeiss EM 10 CA transmission electron microscope at the indicated magnifications.

Surface Plasmon Resonance Experiments

The interaction between SlpA and extracellular matrix components was evaluated by surface plasmon resonance on a BIAcore 3000 instrument. Purified SlpA protein in 5M LiCl was dialyzed against double-distilled water overnight. Monomeric and/or oligomeric protein was separated from self-assembled material by centrifugation at 20,000×g for 20 min. SlpA protein (50 ug/ml in 10 mM Sodium Phosphate pH 7.4) was covalently coupled to CM5 carboxylated dextran chips using N-hydroxysuccinimide (NHS) chemistry. Uncoupled NHS-ester groups were blocked with 1M Ethanolamine, resulting in the coupling of about 1700 resonance units (RU's) to the chip. Kinetic analysis was carried out at 25° C. in 10 mM HEPES, 150 mM NaCl, 3 mM EDTA, 0.005% surfactant P20, pH 7.4. Fibronectin, laminin, fibrinogen and collagen were treated according to manufacturer's instructions and injected at indicated concentrations at a flow rate of 20 ul/min over each flow cell. Binding was determined experimentally by comparing the number of RU's observed as a function of time to an activated and blocked flow cell containing no linked protein. Non-specific binding to the control flow cell appeared insignificant. Data were evaluated using the BIAevaluation 4.1 software. The association and dissociation data were modeled with the BIAevaluation 4.1 software (Pharmacia Biosensor AB). Following subtraction of data from the control flow cell, the binding data produced for the various protein concentrations were fitted simultaneously, assuming the 1:1 Langmuir model. The equilibrium constant for the fibronectin+benzamidine experiment was calculated using steady-state kinetics.

Results

Purification and Crystalline Properties of S-Layer Protein

The *L. brevis* ATCC 8287 SlpA protein has been shown previously to be important for adhesion of the bacterium to human intestinal cell lines [11]. In addition, the protein was shown to display a fibronectin-binding function [11, 61]. To study the crystalline structure of SlpA as well as its interaction with proteinaceous components of the extracellular matrix by surface plasmon resonance, the protein was purified (FIG. 1). Whole cells were treated with 5M LiCl to extract the S-layer. The crude extract after treatment of the cells contained minor impurities, migrating with an apparent molecular mass of 35 and 27 kDa on SDS-PAGE (FIG. 1A, lane 1). Gel filtration chromatography was used to further purify SlpA to a final purity of >95% as judged by SDS-PAGE (FIG. 1, lanes 2 and 3). The purified protein migrates on SDS-PAGE with an apparent molecular mass of 47 kDa, as shown previously [60]. Since S-layer proteins have self-assembly properties, purified SlpA after dialysis was subjected to centrifugation in order to separate self-assembled from soluble protein. This purified protein was used in the subsequent studies outlined below (FIG. 1, lane 3).

Figure 2:
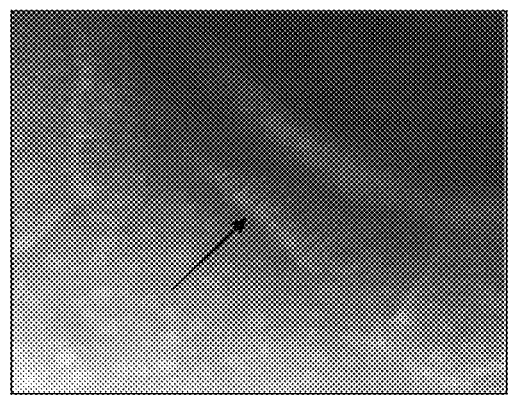
FIG. 2 shows the crystalline Surface layer of whole cells of *L. brevis* (panel A, indicated by arrow, magnification 63,000) or purified SlpA protein (panel B, scale bar 9 nm, magnification 80,000) visualized by negative stain electron microscopy.
Figure 2:
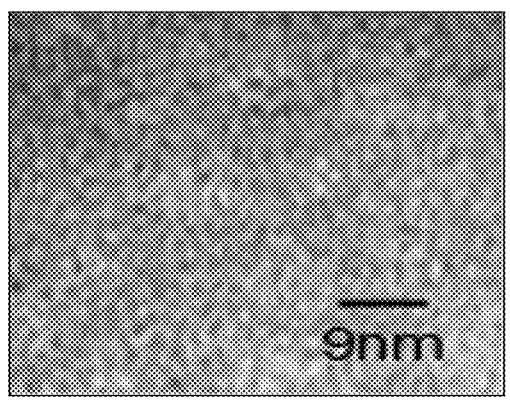

The self-assembly properties and paracrystalline nature of S-layer proteins has facilitated high-resolution analysis using negative stain and freeze-etch electron microscopy. The monomolecular-thick lattices reveal pores of identical size and shape, in the 2 to 8 nm range, with pores occupying up to 70% of the surface. The spacing of individual subunits shows great variation, ranging from 2.5 to 35 nm center-to-center [58,62]. The ultra-structural properties of *Lactobacillus brevis* cells and purified SlpA were examined by negative stain electron microscopy (FIG. 2). Analysis of whole cells clearly revealed S-layer fragments displaying a crystalline proteinaceous layer (FIG. 2A). The purified SlpA protein was examined by negative stain electron microscopy to study its properties in more detail (FIG. 2B). At high magnification, a single layer of individual subunits could be distinguished forming a crystalline protein layer.

Binding of *Lactobacillus brevis* S-Layer Protein to Extracellular Matrix Proteins The involvement of the S-layer in bacteria-host interaction has been described for a variety of microorganisms and has been associated with virulence. Using an elegant flagellar expression system, Hynonen et al identified the SlpA protein of L. brevis ATCC 8287 as an adhesin with affinity for human epithelial cells. In addition, an 81 amino acid fibronectin binding region was identified in the N-terminal region of the protein [11].

Figure 3:
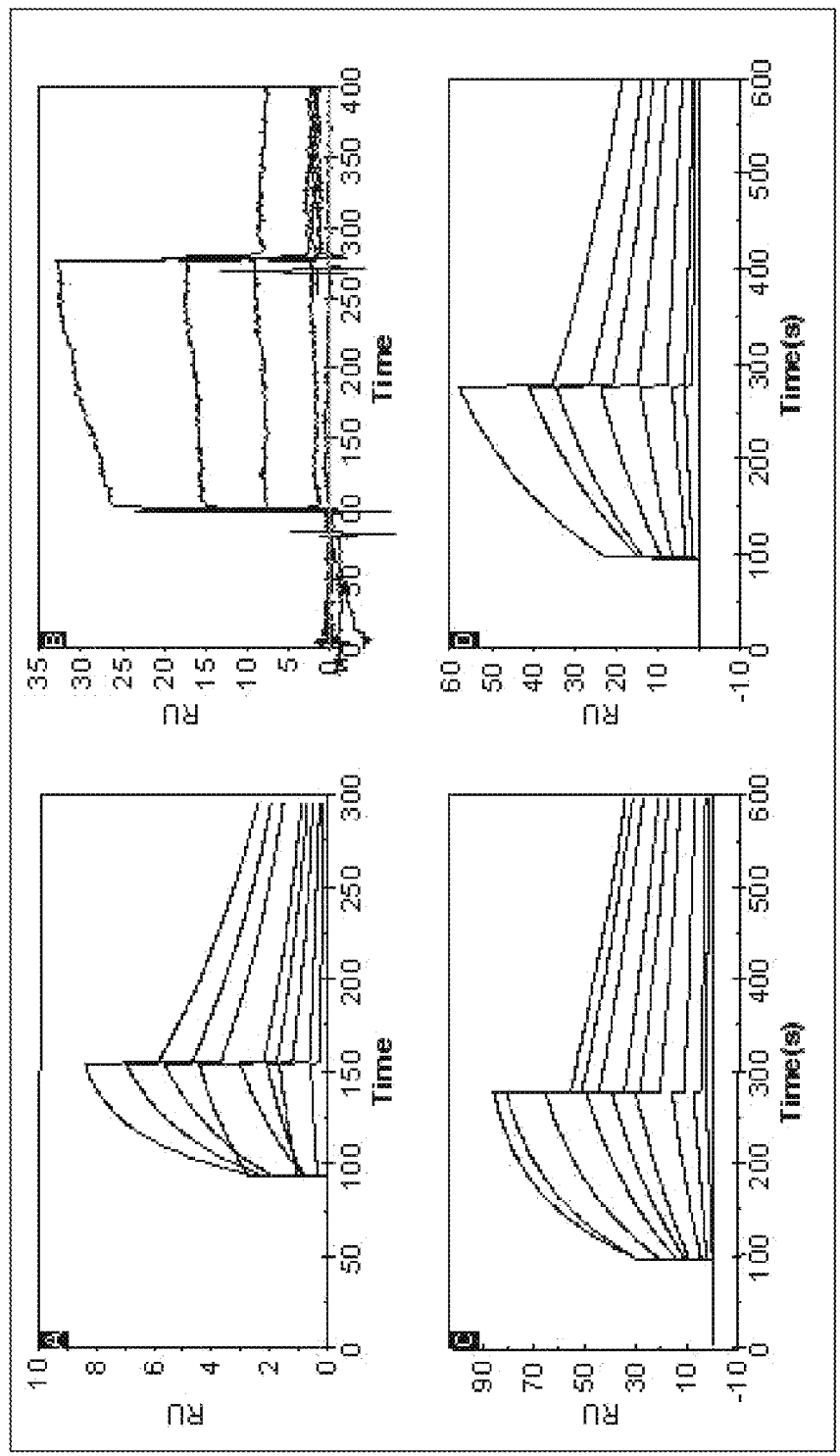
FIG. 3 shows the interaction of SlpA and ECM components fibronectin and laminin measured by surface plasmon resonance. Shown are sensograms of immobilized SlpA protein with fibronectin (panels A and B, 1 mM-10 nM) and laminin (panels C and D, 150 nM-10 nM) in the absence (panels A and C) or presence (panels B and D) of 1 mM Benzamidine.

To examine the binding properties of SlpA to the extracellular matrix proteins fibronectin, laminin, fibrinogen and collagen in detail, surface plasmon resonance was used. FIG. 3 shows the binding of different concentrations of fibronectin (FIG. 3A) and laminin (FIG. 3C) to SlpA. Binding of fibronectin at comparable concentration to laminin resulted in a relatively small response, indicating less fibronectin is bound at the surface implying a lower affinity. The association and dissociation rate constants were estimated from the binding data at different concentrations using the BIAevaluation software and from these values the binding constant was calculated (Table 2). The calculated Kd values were 89.9 nM for fibronectin and 26.7 nM for laminin, indicating a threefold higher affinity of SlpA to bind laminin. In addition, the interaction between SlpA and the ECN components fibrinogen and collagen was studied. The binding constants of SlpA to collagen and fibrinogen were calculated to be 31.8 and 26.1 uM respectively (Table 1), indicating that the binding affinity of SlpA to these two ECM components is three orders of magnitude less than its affinity for fibronectin and laminin.

TABLE 2

Binding characteristics of ECM components to SlpA

|  | $K_d$ | $k_a \times 10^3$ | $k_d \times 10^{-3}$ ($s^{-1}$) |
| --- | --- | --- | --- |
| fibronectin | 89.8 nM | 7.04 | 6.32 |
| laminin | 26.7 nM | 4.89 | 1.3 |
| collagen | 31.8 µM | 3.47 | 1.1 |
| fibrinogen | 485 µM | N.D. | N.D. |
| fibronectin + benzamidine | 30.1 µM | N.D. | N.D. |
| laminin + benzamidine | 66 nM | 3.03 | 2 |

The binding properties of SlpA preincubated with 1 mM benzamidine to fibronectin and laminin were examined (FIGS. 3B and D). The presence of benzamidine resulted in a completely different shape curve for the binding to fibronectin (panel 3A versus 3B), allowing steady state kinetics evaluation only. In the presence of benzamidine, the binding affinity for fibronectin appeared markedly decreased (30.1 uM versus 89.9 nM, Table 2), whereas the binding affinity for laminin appeared relatively unaffected (66 nM versus 26.7 nM, Table 2).

Discussion

S-layer proteins have been identified in many different species of bacteria, and in particular represent a feature common to almost all archaebacteria. They range in size from approximately 40 kDa to 200 kDa, each capable of forming monomolecular lattices of identical subunits [58,59,62]. The interaction of the surface layer protein SlpA of Lactobacillus brevis to fibronectin, laminin, fibrinogen and collagen is described herein. SlpA is shown to interact with high affinity to fibronectin and laminin. Previously, a fibronectin-binding function of the protein was described, located in an 81 amino acid region in the N-terminal region. This region was shown to be required for the interaction of the bacterium with human intestinal cells as well as glass-immobilized fibronectin [11]. No surface adherence could be shown of SlpA to type IV collagen. Although the data presented here clearly indicate an interaction with type IV collagen, the low binding affinity may not have great relevance in vivo, as may be the case for the interaction with fibrinogen. Different S-layer proteins show different affinity for interacting with various ECM components. The CbsA protein of Lactobacillus crispatus was shown to interact with collagens, laminin and lipoteichoic acids [63], whereas Bacillus cereus was shown to adhere to polymorphonuclear leukocytes primarily via type I collagen, fibronectin and laminin [4]. The interaction of B. cereus with fibronectin was suggested to depend on the presence of active protease attached to fibronectin, based on the observation that inhibition of the interaction was observed in the presence of 100 mM benzamidine. Surprisingly, the interaction between SlpA and fibronectin in this study appeared greatly diminished by the presence of 1 mM benzamidine, even in the apparent absence of protease. Benzamidine is highly basic (pKa=11.6), rendering this chemical highly polar [64]. The proposed 81 amino acid SlpA fibronectin-binding region contains a relatively high percentage of tyrosine and arginine residues as compared to the 435 amino acid full length protein. Four out of eight arginines and eight out of twenty-eight tyrosine residues are present in this region. Since arginine plays an important role in many inhibitor/ligand and macromolecular interactions, and since benzamidine is highly polar, the SlpA-fibronectin interaction may be directly inhibited by its presence. In the case of Bacillus cereus, as in this study, the presence of benzamidine inhibited the interaction with fibronectin whereas binding to laminin was relatively unaffected, indicating different binding sites for these two proteins in the S-layer proteins.

Attachment of Surface Proteins to Microspheres

Figure 11:
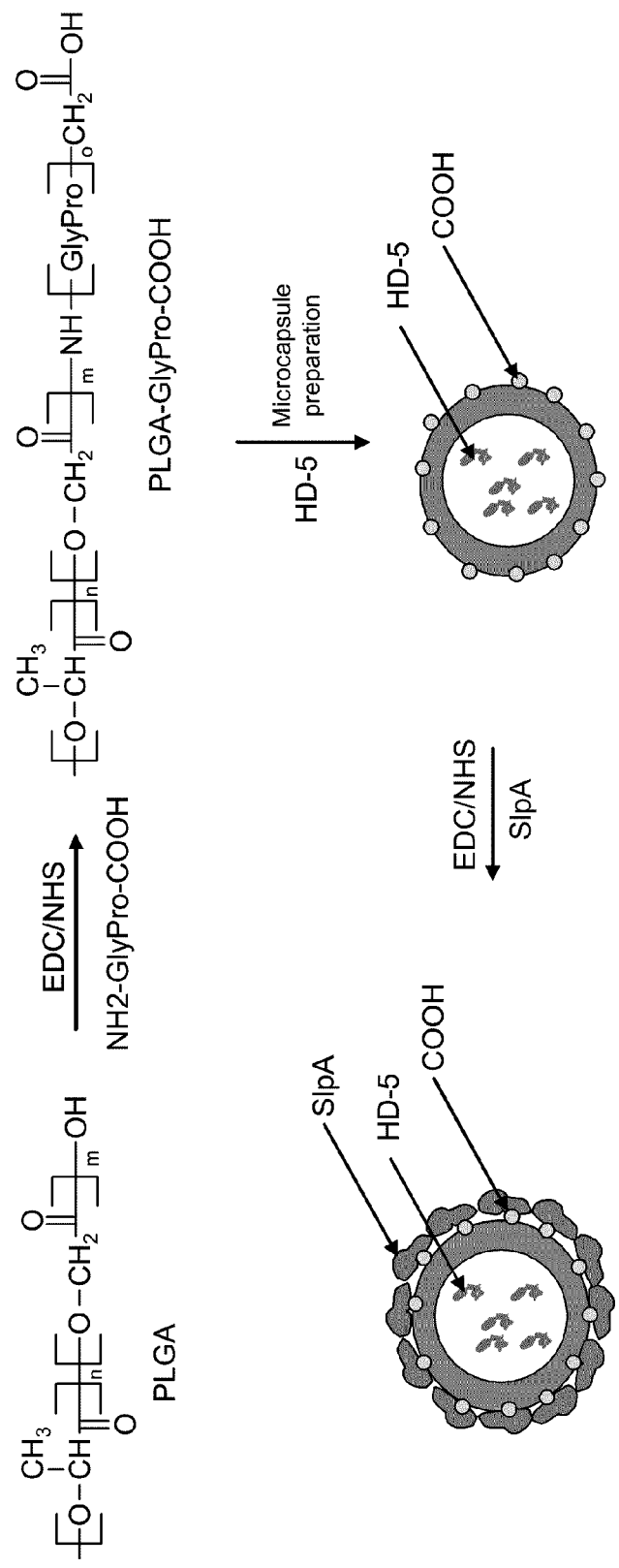
FIG. 11 shows the development of S-layer coated PLGA microspheres. Schematic representation of the synthesis of PLGA-polyGlyPro-COOH co-polymer and microcapsule preparation. Purified amine-functionalized SlpA protein is coupled to the microspheres by carbodiimide coupling chemistry.

FIG. 11 shows the rationale for the covalent attachment of the purified S-layer protein to the microcapsules. The acid group is preactivated to its succinimide by using 1-ethyl-3-(3-dimethylaminopropyl)-carbodiimide (EDC) and reacted with available amino groups of the purified SlpA protein in the presence of N-hydroxysulfosuccinimide (NHS). The size of the particles is preferably evaluated by a Coulter particle counter and size analyzer because particle size is an important parameter, since small particles may be phagocytosed and thus cleared prematurely.

Treatment of inflammatory bowel disease by positively affecting the gut microflora with probiotics has gained increasing interest. Probiotics are live bacteria with health benefits to the host besides nutritional value [65]. Bifidobacteria are considered the most significant beneficial microorganisms, producing antimicrobial agents acting against both gram-negative and gram-positive organisms. Lactobacilli are of benefit also, but are present in lower levels in the human colon. Several mechanisms of action have been shown for probiotics [66-68]: stimulation of the immune response of epithelial cells; antimicrobial activity; enhancing the intestinal barrier function and competition with microbial pathogens for receptors on the epithelium surface. In this respect, the L. brevis SlpA protein and S-layer proteins have potential therapeutic use in intestinal infectious disease, as shown herein.

Examples

Studies Involving HD5α

HD5α Induces Secretion of Interleukin-8 by Intestinal Epithelial Cells

Figure 4:
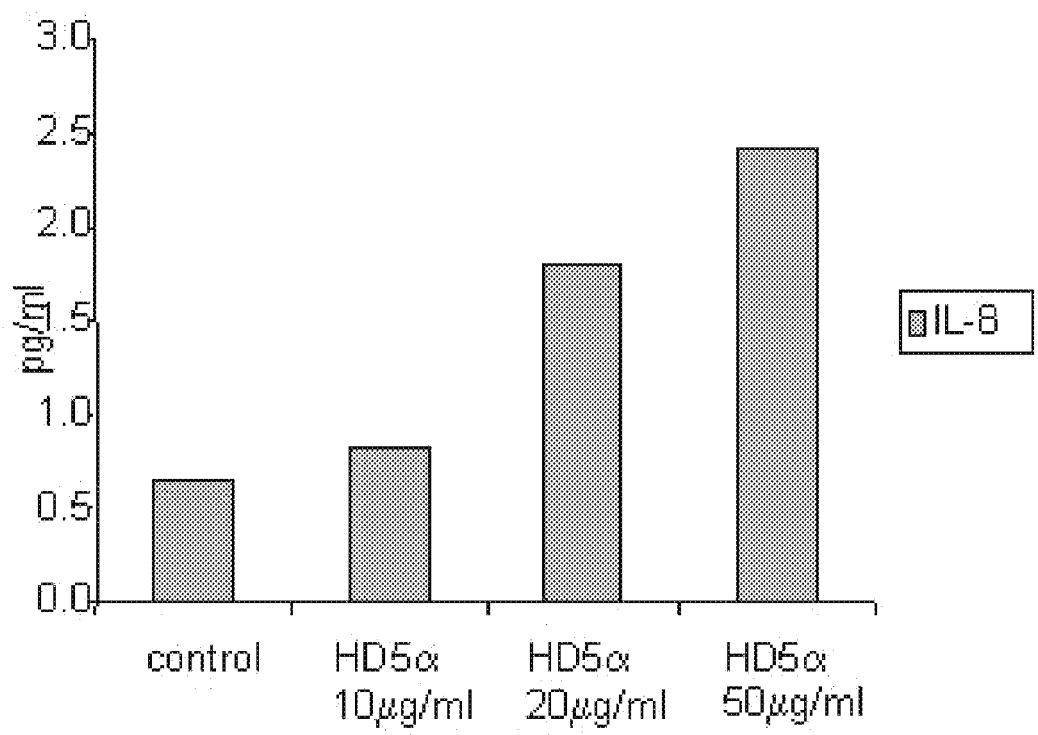
FIG. 4 shows the result of adding HD5α to serum-free culture medium of Caco-2 intestinal epithelial cells at the concentrations indicated. After incubation for 18 h, the culture supernatant was analyzed for secreted IL-8 by ELISA using SEARCHLIGHT™ technology (Pierce), which is an assay that provides a chemiluminescent signal when an included antibody in the assay captures a protein of interest.

Very little is known about the effects of defensin on epithelial cells, which form a single-layer first line of defense and are directly exposed to the intestinal lumen. Therefore, preliminary experiments were carried out in which cultured human intestinal Caco-2 cells were exposed to purified HD5α. Shown in FIG. 4 is the effect of the addition of human defensin 5-α to cultured intestinal epithelial Caco-2 cells on secretion of interleukin-8.

Also, the antibacterial activity and the interaction with intestinal epithelial cells of HD-5α in relation to its structure were studied.

Materials

Chemicals used for solid phase peptide synthesis were obtained as described [90]. *Escherichia coli* ATCC 25922 and *Staphylococcus aureus* ATCC 29213 were from Microbiologics (St. Cloud, Minn.). Caco-2 cell line was obtained from the American Type Culture Collection (Manassas, Va.).

Solid Phase Peptide Synthesis

Chemical synthesis of HD-5 and HD-5Abu, a linear, unstructured form of HD-5 in which the six cysteine residues are replaced by isosteric α-aminobutyric acid (Abu) was carried out as described [18]. Folding of HD-5α was carried out as described [90]. The molecular mass of the peptides was verified by electrospray ionization mass spectrometry (ESI-MS) as described previously [90]. 5-carboxyltetramethyl-rhodamine (Molecular Probes, Eugene, Or) was coupled to HD-5α as follows: 2.0 mg HD-5α was dissolved in 1.0 ml 0.1 M $NaHCO_3$, pH 8.3, 0.2 ml of 5-arboxyltetra-methyl-rhodamine (10 mg/ml in DMSO) and 40 μl di-isopropyl-ethylamine (DIEA) were then added. After stirring for 2 hrs at room temperature, the reaction mixture was filtered and purified by reverse phase HPLC. The molecular mass was verified by ESI-MS as described above.

Antibacterial Activity Assay

The antibacterial activity of HD-5 and HD-5Abu against *E. coli* ATCC 25922 and *S. aureus* ATCC 29213 was carried out in a 96-well turbidimetric assay as described previously [91].

Evaluation of IL-8 Secretion by Caco-2 Cells

Subconfluent monolayers of Caco-2 cells were maintained in RPMI 1640 medium (Gibco), supplemented with 10% FBS (Valley Biomedical, Winchester, Va.), 2 mM L-glutamine (Quality Biological, Gaithersburg, Md.), 20 mM HEPES, 1× nonessential amino acids, 1 mM sodium pyruvate and 5% Penicillin/Streptomycin (Sigma) in a humidified incubator at 37° C. with 5% CO2. Caco-2 cells were used between passages 35-42. Caco-2 cells were plated at a density of $4 \times 10^4$ cells/$cm^2$ in a 96-well plate 48 hours before use. The cells were gently washed twice with serum-free medium and incubated for a further 18 hours in serum-free medium containing the peptides at a final concentration of 50 or 100 ug/ml. Human recombinant tumor necrosis factor alpha (Sigma; 100 ng/ml) was included during incubation with the peptides (100 ug/ml) as indicated. The culture supernatant was collected for measurement of IL-8 using the Luminex-100 system (Bio-rad Laboratories).

Confocal Microscopy

Caco-2 cells (104 cells) were cultured on glass cover slips as described above for 24-48 hours. The cells were washed twice in serum-free medium and incubated with rhodamine-HD5 (10 ∝g/ml) for three hours. After incubation, cells were washed twice with Hanks' Balanced Salt Solution (HBSS). The localization of rhodamine-HD5 on Caco-2 cells was visualized using a Zeiss Laser Scanning Microscope (LSM) 510 system (Carl Zeiss MicroImaging Inc., Thornwood, N.Y.). Fluorescence was excited using a helium-neon laser (543 nm). Emission was passed through a 560 nm long-pass filter prior to acquisition. Optical sections were 1 um thick.

Results

Chemical Synthesis of HD-5 Peptides

Figure 6:
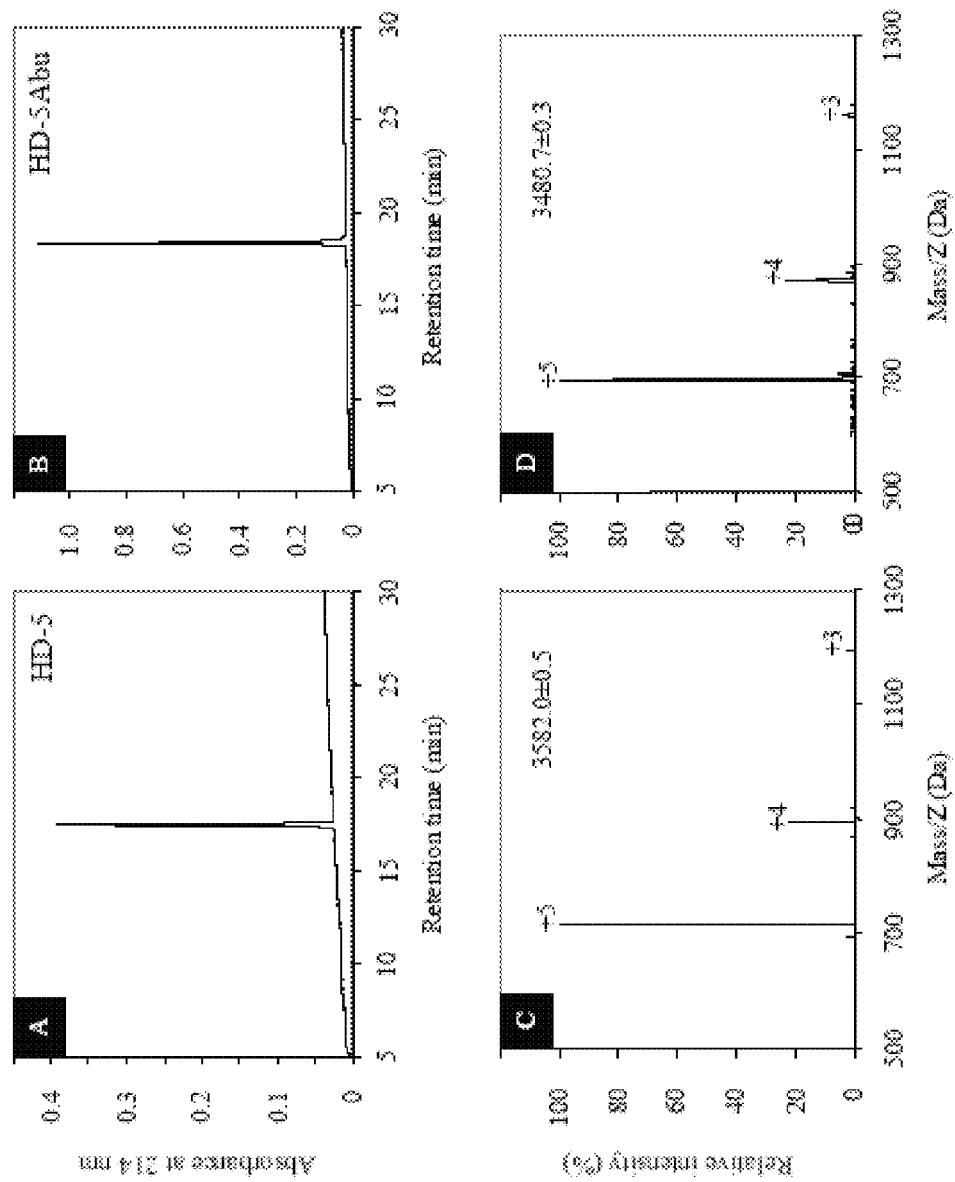
FIG. 6 shows the results of folded and purified HD-5 and HD-5Abu analyzed by reversed phase high performance liquid chromatography (RP-HPLC) and electrospray ionization mass spectrometry (ESI-MS). The HPLC analysis was carried out at 40° C. using a linear gradient of 15-60% (solvent A: water+0.1% TFA; solvent B: acetonitrile+0.1% TFA) at a flow rate of 1 ml/min over 30 min. The determined molecular masses were within experimental error of the expected values based on calculations of the average isotopic compositions.

The HD-5 structure involves three intra-molecular disulfide bonds [90]. To determine the structure of HD-5 in relation to its function, a HD-5 derivative peptide was synthesized, in which the six cysteine residues were replaced with L-(-aminobutyric acid (HD-5Abu), thus preventing the formation of disulfide linkage while leaving the peptide sequence otherwise unaltered. Folded and purified HD-5 and purified HD-5Abu were analyzed on C18 RP-HPLC (FIG. 6, A and B). HD-5 was less hydrophobic than HD-5Abu, as indicated by their relative retention time on C18 RP-HPLC. The molecular mass of both peptides was confirmed by ESI-MS (FIG. 6, C and D). The observed molecular masses of 3582.0±0.5 Da for HD-5α and 3480.7±0.3 Da for HD-5Abu agree with the calculated average isotopic values of 3582.2 and 3480.2 Da respectively.

Antimicrobial Activity of HD-5 Peptides

Figure 7:
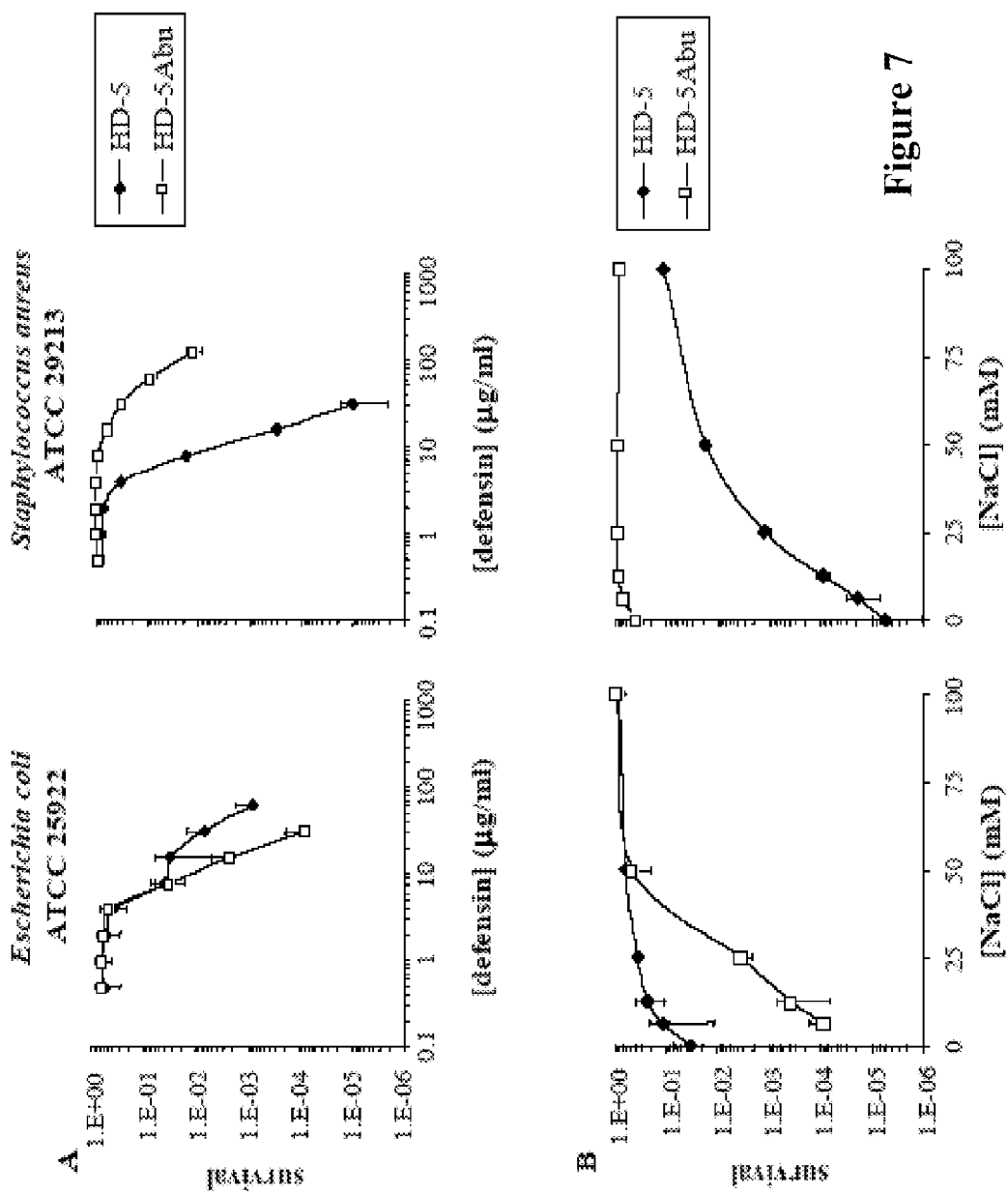
FIG. 7 shows the (A) Survival curves of *E. coli* ATCC 25922 (left) and *S. aureus* ATCC 29213 (right) exposed to HD-5 (filled symbols) or HD-5Abu (open symbols). Strains were exposed to the peptides at concentrations varying two-fold from 0.12 to 125 μg/ml. (B) Strains were exposed to fixed peptide concentrations (100 ug/ml for *E. coli*; 50 ug/ml for *S. aureus*) in the absence or presence of the indicated concentrations of sodium chloride. Each curve is the mean of three separate experiments. Points scored as zero survival could not be plotted.

The antimicrobial activity of both peptides was examined against *E. coli* ATCC 25922 and *S. aureus* ATCC 29213 (FIG. 7A). As described previously [91], HD-5α efficiently killed both bacterial strains and, at comparable peptide concentration, proved more toxic towards *S. aureus* as compared to *E. coli*. At the highest peptide concentration tested (125 ug/ml), *S. aureus* appeared unable to recover from the 2 hour incubation with HD-5α. HD-5Abu was comparable to HD-5α in antimicrobial activity towards *E. coli*, and was even slightly more efficient in killing at higher concentrations. Surprisingly, killing of *S. aureus* by HD-5Abu was four to five orders of magnitude less efficient than killing by HD-5α at comparable peptide concentration.

To evaluate the salt dependence of HD-5α bacterial killing, the antimicrobial assay was performed at increasing sodium chloride concentrations (FIG. 7B). For these experiments, a fixed peptide concentration of 100 ug/ml was used against *E. coli* and 50 ug/ml against *S. aureus*. Increasing salt concentration reduced the antimicrobial activity of HD-5α. At the highest salt concentration tested (100 mM), HD-5α was still significantly toxic against *S. aureus*, whereas antibacterial activity against *E. coli* was almost completely inhibited, even at twice the concentration of peptide. Against *E. coli*, the bactericidal activity of HD-5Abu was significantly inhibited only at a concentration of 50 mM NaCl, inhibition was not increased further by higher salt concentration. Against *S. aureus*, the antibacterial activity of HD-5Abu was completely inhibited even at low salt concentrations. Taken together, these data indicate that effective killing of *E. coli* by HD-5α is structure-independent or alternatively, more sequence-driven. Efficient activity against *S. aureus* requires the peptide to be folded and was less inhibited by increasing salt concentrations.

Interaction of HD-5α Peptides with Intestinal Epithelial Cells

To examine the interaction of HD-5α with Caco-2 cells, rhodamine-labeled HD-5α was synthesized. The molecular mass of the purified peptide was verified by ESI-MS to be 3994.6±0.6 Da, in good agreement with the calculated value of 3994.2 Da (not shown).

Figure 8:
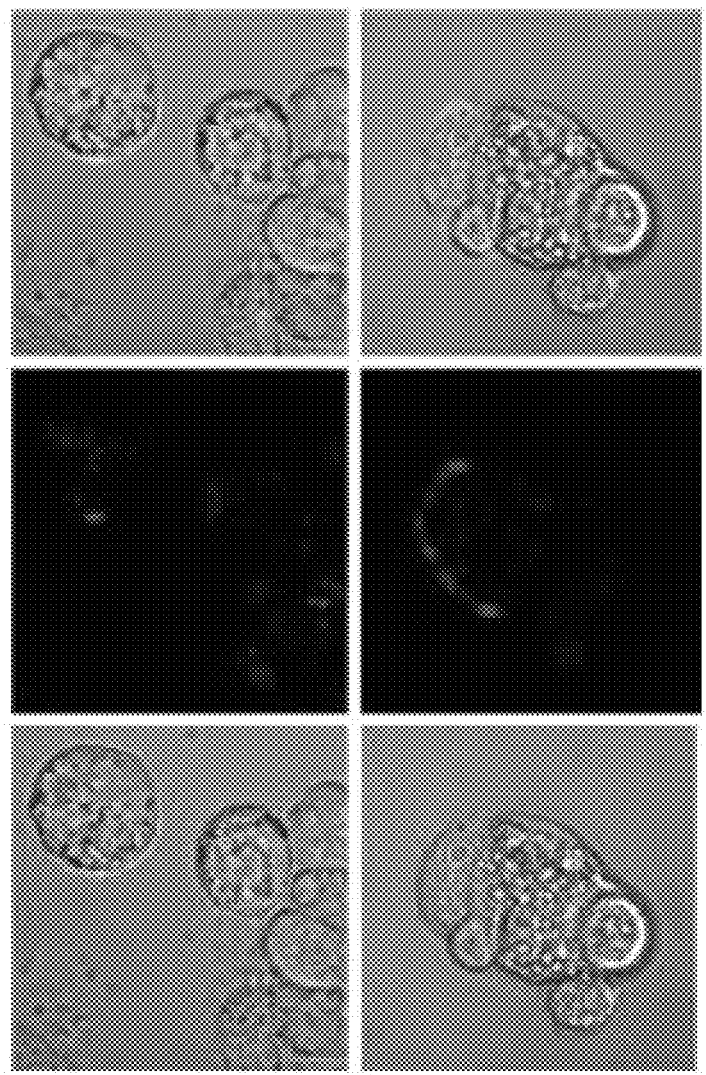
FIG. 8 shows the confocal laser scanning microscopy images of Caco-2 cells incubated with rhodamine-HD-5α. Cells were incubated in serum-free RPMI medium for 3 hours with 10 ug/ml of the peptide and were gently washed twice with HBSS prior to imaging. Left panels show the bright field image, middle panels show the fluorescence image of the rhodamine-labeled peptide, and right panels are a superposition of the two images. The fluorescence image is a 1-um optical section acquired approximately at the equator of the largest cells, which are typically 14-15 um in thickness.
Figure 9:
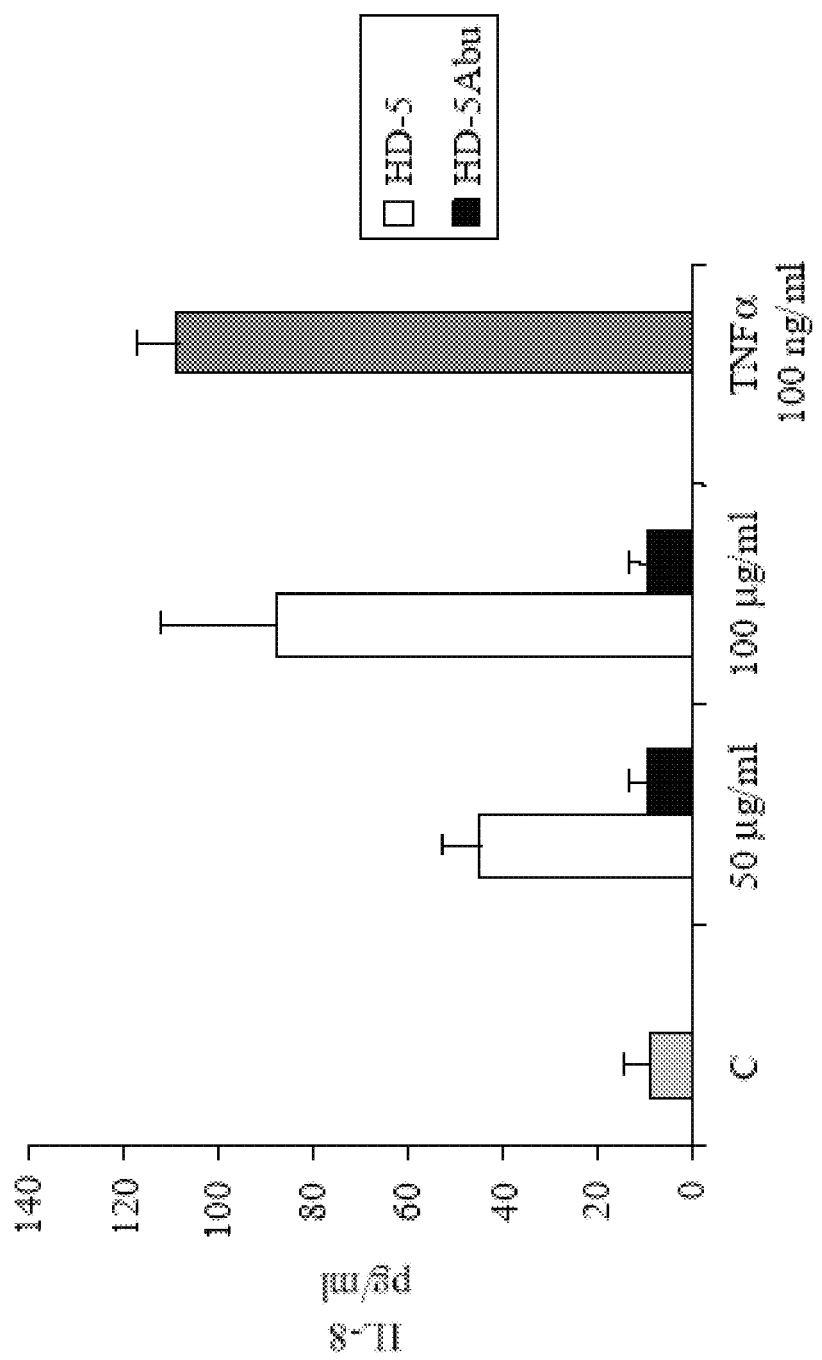
FIG. 9 shows the IL-8 secretion by Caco-2 cells in the absence (light grey bar) or presence of HD-5α (white bars) or HD-5Abu (black bars) at final concentrations of 50 or 100 ∝g/ml. TNFα (100 ng/ml; dark grey bar) served as a positive control. Following incubation for 18 hours, culture supernatants were analyzed for IL-8 using the Luminex-100 system in duplicate. Data represent mean and standard deviation of three individual experiments.

Following incubation of Caco-2 cells with the labeled peptide, localization of HD-5α was visualized by fluorescence confocal microscopy (FIG. 8). While localization of HD-5α was predominantly seen at the surface of the Caco-2 cells, internalization of the probe was also observed. To test whether HD-5α induces an intestinal inflammatory response, Caco-2 intestinal epithelial cells were incubated in the presence of increasing concentrations of the peptide. Steady-state quantities of secreted HD-5 have been estimated to be in the range of 50-250∝g/ml in the intestinal lumen [92,93]. Therefore, the effects of the peptides were examined at concentrations of 50 and 100 ug/ml. Cells incubated with 100 ng/ml tumor necrosis factor (TNFα) were used as a positive control. HD-5α induced IL-8 secretion in a dose-dependent fashion (FIG. 9, white bars). IL-8 levels increased ~10-fold at a peptide concentration of 100 ug/ml compared to control cells, similar to IL-8 levels observed after incubation with TNFα (FIG. 9, grey bar). To examine the effect of peptide structure, cells were incubated with the same concentration of the HD-5Abu peptide. Induction of IL-8 secretion was not observed in the presence of HD-5Abu at the same concentrations (FIG. 9, black bars), indicating the induction of IL-8 secretion depends on the structure of HD-5α.

Figure 10:
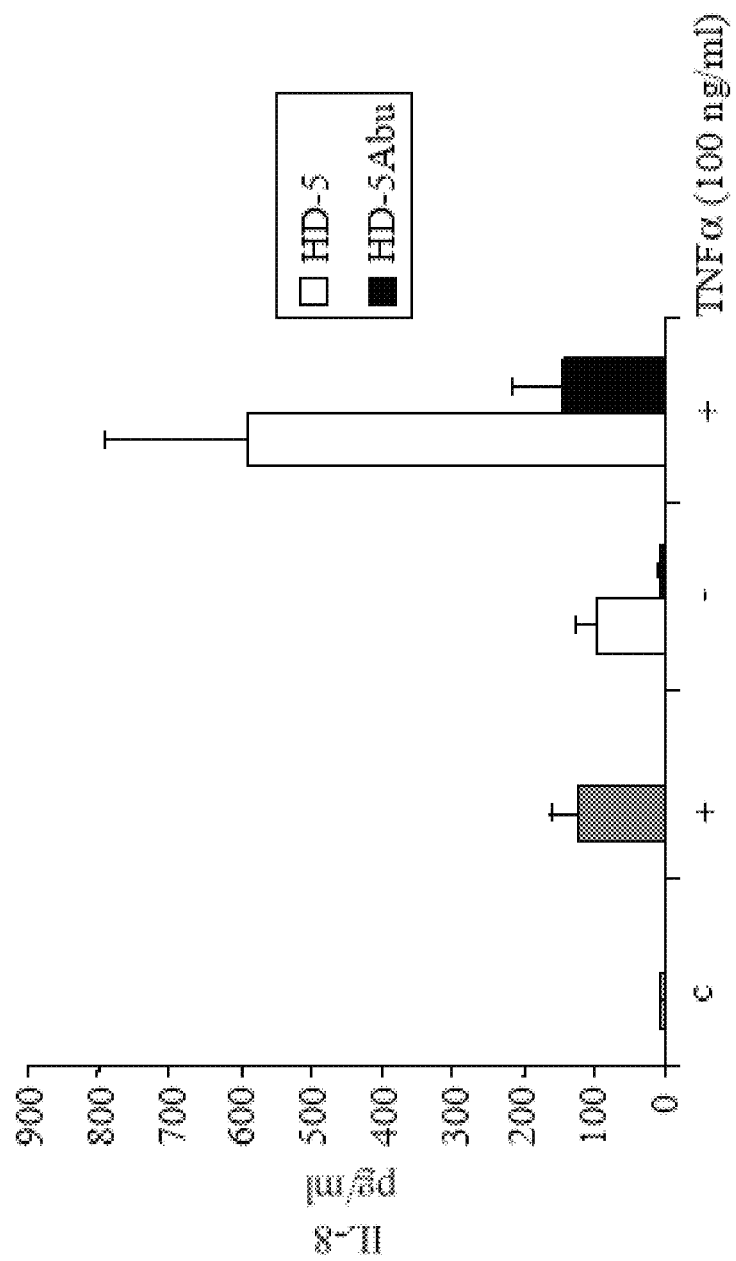
FIG. 10 shows IL-8 secretion by Caco-2 cells in the presence of HD-5 (100 ug/ml; white bars) or HD-5Abu (100 ∝g/ml; black bars), with and without TNFα (100 ng/ml) as indicated. No peptides (c) and TNFα alone (dark grey bar) served as controls. Following incubation for 18 hours, culture supernatants were analyzed for IL-8 using the Luminex-100 system in duplicate. Data represent mean and standard deviation of three individual experiments.

In addition to HD-5α, TNFα is also expressed by Paneth cells [94]. Therefore, the IL-8 secretion upon co-incubation of intestinal epithelial cells with HD-5α and TNFα (FIG. 10) was examined. Incubation with HD-5α or TNFα, alone increased IL-8 secretion ~10-fold relative to the control. Co-incubation of HD-5α and TNFα resulted in an additional 6-fold increase in IL-8 secretion as compared to the levels observed when the two agents were applied separately. In contrast, HD-5Abu was completely ineffective in stimulating IL-8 secretion. Together, these data suggest that HD-5α and TNFα enhance IL-8 secretion by intestinal epithelial cells synergistically, and that HD-5α must be structured to stimulate secretion.

The result show that killing of *E. coli* by HD-5α is independent of peptide structure, whereas antimicrobial activity against *S. aureus* requires the native structure and it was shown herein that HD-5α induces secretion of IL-8 by epithelial cells in a structure dependent manner. Furthermore, HD-5 and TNFα act synergistically to induce secretion.

Importantly, approximately one-third of Crohn's disease patients show a further reduced expression of HD-5α. Based on the results shown herein, lower levels of HD-5 observed in Crohn's disease patients compared to normal conditions may compromise the ability of the intestinal epithelium to respond to immune challenges by weakening the antibacterial activity as well as by weakening the immune response of the epithelium.

HD5α can be fluorescently labeled successfully.

Figure 5:
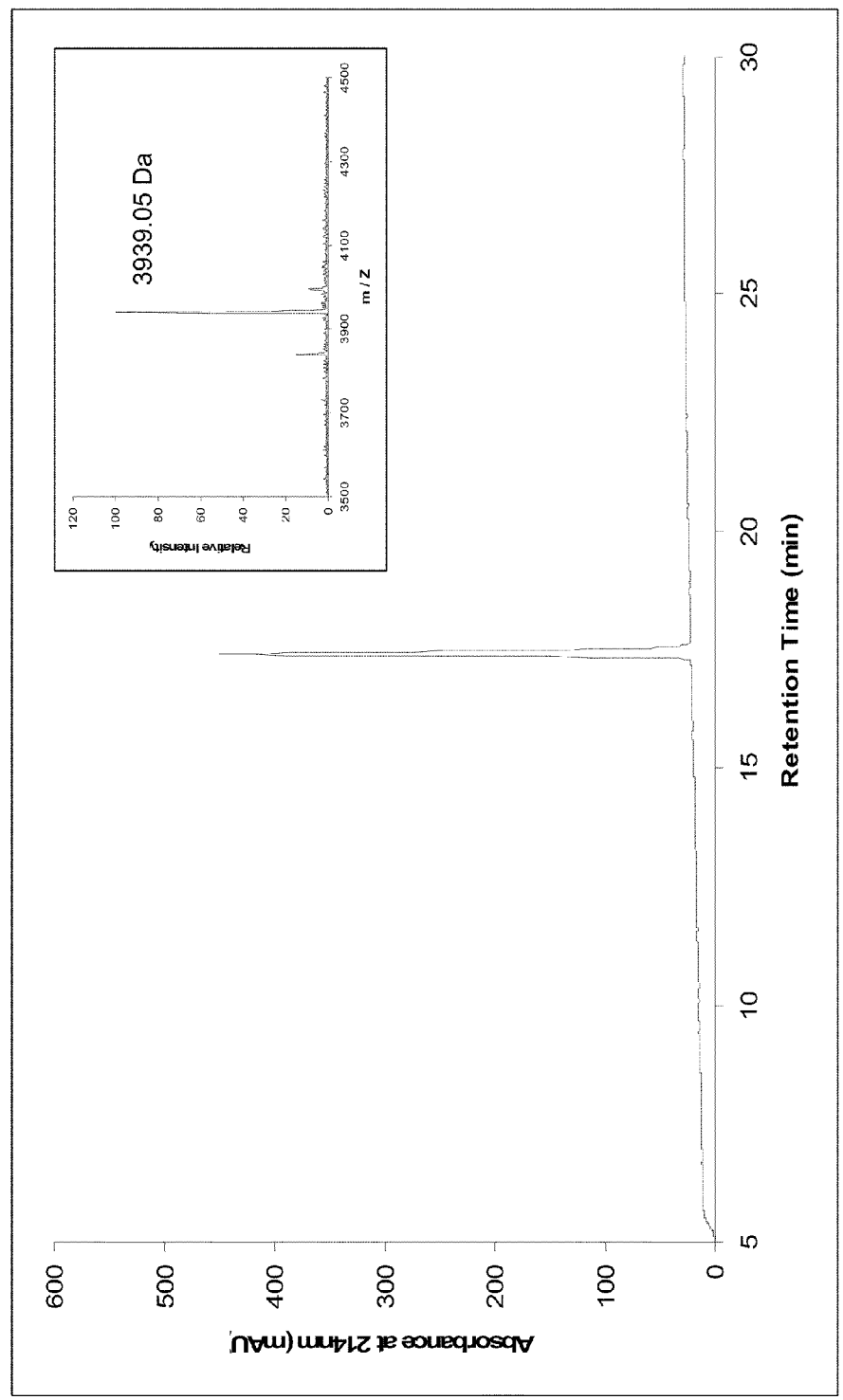
FIG. 5 shows folded and purified FITC-labeled HD5α analyzed by reversed phase HPLC and ESI-MS.

Since the N-terminal α-amino group is the only reactive group in HD5α, fluorescein isothiocyanate (FITC) was directly coupled to folded HD5α in solution using a succinimide ester-activated fluorophore (commercially available) to react with the amino group. Shown in FIG. 5 is the HPLC trace of FITC-labeled HD5α together with the mass determination.

Site-Specific Labelling of HD5α and HBD-2 with Photo-Cross Linking or Fluorescent Groups HD5α and HBD-2 site-specifically labeled with photo-cross linking or fluorescent groups. For fluorescent labeling, two techniques are in practice—site-specific labeling on solid phase during peptide synthesis and non-specific labeling in solution on a folded protein. A succinimide ester-activated fluorophore (commercially available) reacting with the amino group(s) on a target molecule is arguably the most robust chemistry. Since the N-terminal α-amino group is the only reactive group in HD5α, FITC was directly coupled to folded HD5α in solution successfully. For HBD2, N-terminal labeling will be carried out on resin before the peptide is deprotected, cleaved and folded as hBD2 contains multiple Lysine residues that effectively preclude controlled labeling in solution.

Photo-cross-linking reagents are frequently used for identifying the targets of protein/peptide ligands and for mapping the binding site on the target molecule [70]. In a typical photo-cross-linking reaction, the formation of covalent linkage between the photoreactive group and the receptor protein can be initiated by controlled irradiation of the photophore at a defined wavelength. Therefore, by chemically attaching a photophore to the ligand of interest, a covalent complex with the receptor protein can be produced. For photo-cross linking, 4-benzoyl-phenylalanine (Bpa) is one of the most widely used photophores due to its highly efficient and specific photoreactivity and stability (single-site on C—H bonds) [71]. As an unnatural amino acid, it can be incorporated into peptides using the standard chemistry for solid phase peptide synthesis. The photophore is suitably conjugated with a tag molecule for easy detection, using radioactive, fluorescent or immunoreactive moieties. When biotin is attached to the photophore, immobilized avidin affords efficient affinity separation of the ligand-receptor complexes.

The rationale for the design is as follows. Biotin as an affinity handle will be used to immobilize defensin-receptor complexes to avidin-Sepharose beads. This will facilitate efficient removal of non-specifically bound species and allow for enrichment of receptor molecules. The role for Lys is two-fold. It serves as a spacer between Bpa, biotin and defensin that minimizes potential steric hindrance for binding and photoreaction. It also provides a carboxyl group for specifically attaching to defensin. Three precursors: Boc-Bpa-OH, Boc-Lys(Fmoc)-OH and activated Biotin (succinimidyl ester) are all available commercially. The three compounds will be attached sequentially to the N-terminus of defensin using standard Boc chemistry for solid phase peptide synthesis.

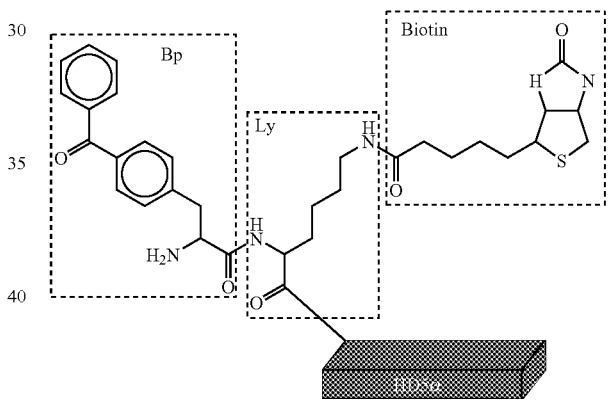

Examples

S-layer Coated Biodegradable Microcapsules Containing Human Defensin 5

The immunomodulatory properties of human defensin 5α are suggestive of its utility as a molecular therapeutic in the treatment of inflammatory gut diseases, such as Crohn's disease of the ileum. As such, HD5α is encapsulated by biodegradable microcapsules coated with the purified Surface layer (S-layer) protein SlpA from *Lactobacillus brevis*. This coating specifically targets the microcapsules to intestinal epithelial cells through the affinity of the S-layer protein for extra cellular membrane components. This novel concept ensures defensins to reach their site of action.

HD5α or derivatives of interest are microencapsulated by a (water-in-oil)-in water solvent extraction technique in a simple beaker/stirrer setup, using Poly(DL-lactide-co-glycolide) as the polymer [80,81]. The size of the resulting microcapsules depends mainly on the polymer used and the speed of preparation of the emulsion.

Many studies in development of biodegradable carriers have employed a "dope and hope" strategy. Encapsulated antigens are administered by oral gavage in the hope that a proportion is transported to immune effector sites at the intestinal epithelium. Using the technology developed herein, specific targeting of the encapsulated defensins to their immune effector sites is ensured by coating of the microcapsules with the purified SlpA protein from *Lactobacillus brevis* ATCC 8287.

The microcapsules are characterized by size using a Coulter counter as well as electron microscopy. The interaction between the microparticles and intestinal cells are visualized by microscopic analysis. In addition, the interaction between the S-layer protein and ECM components are studied by surface plasmon resonance experiments. The efficiency of encapsulation of the defensins can be judged by HPLC analysis by comparing the HPLC peak surface from the input peptides to that of the microcapsules. The rate of release over time of the defensins can be judged by HPLC also after rehydration of the lyophilized particles. In all these studies, microcapsules without protein are used as a control. The antimicrobial properties of all HD5α derivatives proposed in this work will be tested using a "virtual colony counting" approach, an in-house 96-well turbidimetric assay that allows rapid screening of the antimicrobial activity of many samples.

The novel concept of biodegradable polymers coated with the S-layer protein provides for the delivery of these microcapsules as antigen carriers specifically targeting epithelial cells both in vitro and in vivo.

REFERENCES

The contents of all references cited herein are hereby incorporated by reference herein for all purposes.

[1] Navarre, W. W. and Schneewind, O. (1999) Surface proteins of gram-positive bacteria and mechanisms of their targeting to the cell wall envelope. Microbiol. Mol. Biol. Rev. 63, 174-229.

[2] Engelhardt, H and Peters, J. (1998) Structural research on surface layers: a focus on stability, surface layer homology domains and surface layer-cell wall interactions. J. Struct. Biol. 124, 276-302.

[3] Baumeister, W., Wildhaber, I. and Phipps, B. M. (1989) Principles of organization in eubacterial and archaebacterial surface proteins. Can. J. Microbiol 35, 215-227.

[4] Kotiranta, A., Haapasalo, M., Kari, K., Kerosuo, E., Olsen, I., Sorsa, T., Meurman, J. H. and Lounatmaa, K. (1998) Surface structure, hydrophobicity, phagocytosis and adherence to matrix proteins of *Bacillus cereus* cells with and without the crystalline surface protein layer. Inf. Immun. 66, 4895-4902.

[5] Thompson, S. A. (2002) *Campylobacter* surface-layers (S-layers) and immune evasion. Ann. Periodontol. 7, 43-53.

[6] Sabet, M., Lee, S. W., Nauman, R. K., Sims, T. and Um, H. S. (2003) The surface (S-) layer is a virulence factor of *Bacteroides forsythus*. Microbiology 149, 3617-3627.

[7] Esteve, C., Alcaide, E., Canals, E., Merino, S., Blasco, D., Figueras, M. J. and Tomas, J. M. (2004) Pathogenic *Aeromonas hydrophila* serogroup O:14 and O:81 strains with an S layer. Appl. Environ. Microbiol. 70, 5898-5904.

[8] McCracken, V. J. and Lorenz, R. G. (2001) The gastrointestinal ecosystem: a precarious alliance among epithelium immunity and microbiota. Cell Microbiol. 3, 1-11.

[9] Freje J., Kos, B., Svetec, I. K., Zgaga, Z., Mrsa, V. and Suskovic, J. (2005) Importance of S-layer proteins in probiotic activity of *Lactobacillus acidophilus* M92. J. Appl. Microbiol. 98, 285-292.

[10] Horie, M., Ishiyama, A., Fujihira-Ueki, Y., Sillanpäa, J., Korhonen, T. K. and Toba, T. (2002) Inhibition of the adherence of *Escherichia coli* strains to basement membrane by *Lactobacillus crispatus* expressing an S-layer. J. Appl. Microbiol. 92, 396-403.

[11] Hynönen, U., Westerlund-Wikström, B., Palva, A. and Korhonen, T. K. (2002) Identification by flagellum display of an epithelial cell- and fibronectin-binding function in the SlpA surface protein of *Lactobacillus brevis*. J. Bacteriol. 184, 3360-3367.

[12] Sára, M. and Sleytr, U. B. (2000) S-layer proteins. J. Bacteriol. 182, 859-868.

[13] Beveridge T. J., Pouwels, P. H., Sára, M., Kotiranta, A., Lounatmaa, K., Kari, K., Kerosuo, E., Haapsalo, M., Egelseer, E. M., Schocher, I., Sleytr, U. B., Morelli, M., Callegari, M. L., Nomenelli, J. F., Bingle, W. H., Smit, J., Leibovitz, E., Lemaire, M., Miras, I., Salamitou, S., Beguin, P., Ohayon, H., Gounon, P., Matuschek, M. and Koval, S. F. (1997) Functions of S-layers. FEMS Microbiol. Rev. 20, 99-149.

[14] Rakoff-Nahoum, S., Paglino, J., Eslami-Varzaneh, F., Edberg, S. and Medzhitov, R. (2004) Cell 118, 229-241.

[15] Russell, M. W. and Mestecky, J. (2002) Microbes Infect. 4, 667-677.

[16] Shikina, T., Hiroi, T., Iwatani, K., Jang, M. H., Fukuyama, S., Tamura, M., Kubo, T., Ishikawa, H. and Kiyono, H. (2004) J. Immunol. 172, 6259-6264.

[17] Neutra, M. R., Pringault, E. and Kraehenbuhl, J. P. (1996) Annu. Rev. Immunol. 14, 275-300.

[18] Janeway, C. A. Jr., and Medzhitov, R. (2002) Annu. Rev. Immunol. 20, 197-216.

[19] Gordon, S. (2002) Cell 111, 927-930.

[20] Akira, S. and Takeda, K. (2004) Nat. Rev. Immunol. 4, 499-511.

[21] Chamaillard, M., Girardin, S. E., Vialla, J. and Philpott, D. J. (2003) Cell Microbiol. 5, 581-592.

[22] Hoffmann. J. A, Kafatos, F. C., Janeway, C. A. and Ezekowitz, R. A. (1999) Science 284, 1313-1318.

[23] Zhang, D., Zhang, G., Hayden, M. S., Greenblatt, M. B., Bussey, C., Flavell, R. A. and Ghosh, S. (2004) Science 303, 1522-1526.

[24] Heil, F., Hemmi, H., Hochrein, H., Ampenberger, F., Kirschning, C., Akira, S., Lipford, G., Wagner, H. and Bauer, S. (2004) Science 303, 1526-1531.

[25] Alexopolou, L., Holt, A. C., Medzhitov, R. and Flavell, R. A. (2001) Nature 413, 732-738.

[26] Hayashi, F., Smith, K. D., Ozinsky, A., Hawn, T. R., Yi, E. C., Goodlett, D. R., Eng, J. K., Akira, S., Underhill, D. M. and Aderem, A. (2001) Nature 410, 1099-1103.

[27] Hemmi, H., Takeuchi, O., Kawai, T., Kaisho, T., Sato, S., Sanjo, H., Matsomoto, M., Hoshino, K., Wagner, H., Takeda, K. and Akira, S. (2000) Nature 408, 740-745.

[28] Matsumoto, M., Funami, K., Tanabe, M., Oshiumi, H., Shingai, M., Seto, Y., Yamamoto, A. and Seya, T. (2003) J. Immunol. 171, 3154-3162.

[29] Lund, J., Sato, A., Akira, S., Medzhitov, R. and Iwasaki, A. (2003) J. Exp. Med. 198, 513-520.

[30] Eckmann, L. and Karin, M. (2005) Immunity 22, 661-667.

[31] Fellerman, K., Wehkamp, J., Herrlinger, K. R. and Stange, E. F. (2003) Eur. J. Gastroenterol. Hepatol 15, 627-634.

[32] Grimm, M. C. and Pavli, P. (2004) Gut 53, 1558-1560.

[33] Kelly, P., Feakins, R., Domizio, P., Murphy, J., Bevins, C., Wilson, J., McPhail, G., Poulsom, R. and Dhaliwal, W. (2004) Clin. Exp. Immunol. 135, 303-309.
[34] Bevins, C. L., Martin-Porter, E. and Ganz, T. (1999) Gut, 45, 911-915.
[35] Oppenheim, J. J., Biragyn, A., Kwak, L. W. and Yang, D. (2003) Ann. Rheum. Dis 62, 17-21.
[36] Cunliffe, R. N. (2003) Mol. Immunol. 40, 463-467.
[37] Lehrer, R. I. and Ganz, T. (1999) Curr. Opin. Immunol. 11, 23-27.
[38] Ganz, T. and Lehrer, R. I (1998) Curr. Opin. Immunol. 10, 41-44.
[39] Zasloff, M. (2002) Nature, 415, 389-395.
[40] Jones, D. E. and Bevins, C. L. (1992) J. Biol. Chem. 267, 23216-23225.
[41] Jones, D. E. and Bevins, C. L. (1993) FEBS Lett. 315, 187-192.
[42] Daher, K. A., Selsted, M. E. and Lehrer, R. I. (1986) J. Virol. 60, 1068-1074.
[43] Lichtenstein, A., Ganz, T., Selsted, M. E. and Lehrer, R. I. (1986) Blood 68, 1407-1410
[44] Ganz, T. (2003) Nat. Immunology 3, 710-720.
[45] Territo, M. C., Ganz, T., Selsted, M. E. and Lehrer, R. I. (1989) J. Clin. Invest. 84, 2017-2020.
[46] Yang, D., Chen, Q., Chertov, O. and Oppenheim, J. J. (2000) J. Leukoc. Biol. 68, 9-14.
[47] Chertov, O., Michiel, D. F., Xu, L., Wang, J. M., Tani, K., Murphy, W. J., Longo, D. L., Taub, D. D. and Oppenheim, J. J. (1996) J. Biol. Chem. 271, 2935-2940.
[48] Yang, D., Chertov, O., Bykovskaia, S. N., Chen, Q., Buffo, M. J., Shogan, J., Anderson, M., Schroder, J. M., Wang, J. M., Howard, O. M. and Oppenheim, J. J. (1999) Science 286, 525-528.
[49] Yang, D., Chertov, O., and Oppenheim, J. J. (2001) J. Leukoc. Biol. 69, 691-697.
[50] Biragyn, A., Ruffini, P. A., Leifer C. A., Klyushnenkova, E., Shakhov, A., Chertov, O., Shirakawa, A. K., Farber, J. M., Segal, D. M., Oppenheim, J. J. and Kwak, L. W. (2002) Science 298, 1025-1029.
[51] Fernandez, E. J. and Lolis, E. (2002) Annu. Rev. Pharmacol. Toxicol. 42, 469-499.
[52] Hugot, J. P., Chamaillard, M., Zouali, H., Lesage, S., Cezard, J. P., Belaiche, J., Almer, S., Tysk, C., O'Morain, C. A., Gassull, M., Binder, V., Finkel, Y., Cortot, A., Modigliani, R., Laurent-Puig, P., Gower-Rousseau, C., Macry, J., Colombel, J. F., Sahbatou, M. and Thomas, G. (2001) Nature 411, 599-603.
[53] Ogura, Y., Bonen, D. K., Inohara, N., Nicolae, D. L., Chen, F. F., Ramos, R., Britton, H., Moran, T., Karaliuskas, R., Duerr, R. H., Achkar, J. P., Brant, S. R., Bayless, T. M., Kirschner, B. S., Hanauer, S. B., Nunez, G. and Cho, J. H. (2001) Nature 411, 603-606.
[54] Ogura, Y., Inohara, N., Benito, A., Chen, F. F., Yanaoka, S. And Nunez, G. (2001) J. Biol. Chem. 276, 4812-4818.
[55] Lala, S., Ogura, Y., Osborne, C., Hor, S. Y., Bromfield, A., Davies, S., Ogunbiyi, O., Nunez, G. And Flavell, R. A. (2003) Gastroenterol. 125, 47-57.
[56] Girardin, S. E., Boneca, I. G., Viala, J., Chamaillard, M., Labigne, A., Thomas, G., Philpott, D. J. and Sansonetti, P. J. (2003) J. Biol. Chem. 278, 8869-8872.
[57] Inohara, N., Ogura, Y., Fontalba, A., Gutierrez, O., Pons, F., Crespo, J., Fukase, K., Inmura, S., Kusumoto, S., Hashimoto, M., Foster, S. J., Moran, A. P., Fernandez-Luna, J. L. and Nunez, G. (2003) J. Biol. Chem. 278, 5509-5512.
[58] Inohara, N., Chamaillard, M., McDonald, C. And Nunez, G. (2004) Annu. Rev. Biochem. 74, 355-383.
[59] Kobayashi, K. S., Chamaillard, M., Ogura, Y., Henegariu, O., Inohara, N., Nunez, G. And Flavell, R. A. (2005) Science 307, 731-734.
[60] Sampathkumar, P. and Gilchrist, M. L. (2004) Synthesis and characterization of bioconjugates of S-layer proteins. Bioconjugate Chem. 15, 685-693.
[61] Avall-Jaaskelainen, S., Lindholm, A. and Palva, A. (2003) Surface display of the receptor-binding region of the *Lactobacillus brevis* S-layer protein in *Lactococcus lactis* provides nonadhesive lactococci with the ability to adhere to intestinal epithelial cells. Appl. Environ. Microbiol. 68, 5943-5951.
[62] Sleytr, U. B. and Beveridge, T. J. (1999) Bacterial S-layers. Trends in Microbiol. 7, 253-260.
[63] Antikainen, J., Anton, L., Sillanpää, J. and Korhonen, T. K. (2002) Domains in the S-layer protein CbsA of *Lactobacillus crispatus* involved in adherence to collagens, laminin and lipoteichoic acids and in self-assembly. Mol. Microbiol. 46, 381-394.
[64] Lam, P. Y. S., Clark, C. G., Li, R., Pinto, D. J. P., Orwat, M. J., Galemmo, R. A., Fevig, J. M., Teleha, C. A., Alexander, R. S., Smallwood, A. M., Rossi, K. A., Wright, M. R., Bai, S. A., He, K., Luettgen, J. M., Wong, P. C., Knabb, R. M. and Wexler, R. R. (2003) Structure-based design of novel guanidine/benzamidine mimics: potent and orally bioavailable factor Xa inhibitors as novel anticoagulants. J. Exp. Med. 46, 4405-4418.
[65] Rastall, R. A. and Maitin, V. (2002) Prebiotics and synbiotics towards the next generation. Curr. Opin. Biotechnol. 13, 490-498.
[66] Fedorak, F. N. and Madsen, K. L. (2004) Probiotics and the management of inflammatory bowel disease. Inflamm. Bowel Dis. 10, 286-299.
[67] Sartor, R. B. (2005) Probiotic therapy of intestinal inflammation and infections. Curr. Opin. Gastroenterol. 21, 44-50.
[68] Dotan, I. and Rachmilevitz, D. (2005) Probiotics in inflammatory bowel disease: possible mechanisms of action. Curr. Opin. Gastroenterol. 21, 426-430.
[69] Avall-Jaaskelainen, S. and Palva, A. (2005) *Lactobacillus* Surface layers and their applications. FEMS Microbiol. Rev. 29, 511-529.
[70] Dorman, G. and Prestwich, G. D. (2000) Trends Biotechnol. 18, 64-77.
[71] Bremer, A. A., Leeman, S. E. and Boyd, N. D. (2001) J. Biol. Chem. 276, 22857-22861.
[72] Chait, B. T. and Kent, S. B. (1992) Science 257, 1885-1894.
[73] Mann, M., Hendrickson, R. C. and Pandey, A. (2001) Annu. Rev. Biochem. 70, 437-473.
[74] Fellerman, K., Wehkamp, J., Herrlinger, K. R. and Stange, E. F. (2003) Eur. J. Gastroenterol. Hepatol 15, 627-634.
[75] Grimm, M. C. and Pavli, P. (2004) Gut 53, 1558-1560.
[76] Kelly, P., Feakins, R., Domizio, P., Murphy, J., Bevins, C., Wilson, J., McPhail, G., Poulsom, R. and Dhaliwal, W. (2004) Clin. Exp. Immunol. 135, 303-309.
[77] Ganz, T. (2003) Nat. Immunology 3, 710-720.
[78] Oppenheim, J. J., Biragyn, A., Kwak, L. W. and Yang, D. (2003) Ann. Rheum. Dis. 62, 17-21.
[79] Kobayashi, K. S., Chamaillard, M., Ogura, Y., Henegariu, O., Inohara, N., Nunez, G. And Flavell, R. A. (2005) Science 307, 731-734.
[80] Foster, N. and Hirst, B. H. (2005) Adv. Drug Del. Rev. 57, 431-450.
[81] Sinha, V. R. and Trehan, A. (2005) J. of Contr. Rel. 90, 261-280.

[82] Avall-Jaaskelainen, S. Lindholm, A. and Palva, A. (2003) Appl. Env. Microbiol. 69, 2230-2236.
[83] Sleytr, U. B. and Beveridge, T. J. (1999) Tr. In Microbiol. 7, 253-260.
[84] Sára, M. and Sleytr, U. B. (2000) J. Bac. 182, 859-868.
[85] Rakoff-Nahoum, S., Paglino, J., Eslami-Varzaneh, F., Edberg, S. and Medzhitov, R. (2004) Cell 118, 229-241.
[86] Biragyn, A., Ruffini, P. A., Leifer C. A., Klyushnenkova, E., Shakhov, A., Chertov, O., Shirakawa, A. K., Farber, J. M., Segal, D. M., Oppenheim, J. J. and Kwak, L. W. (2002) Science 298, 1025-1029.
[87] Chen, H., Xu, Z., Xu, N. and Cen, P. (2005) J. Biotechnol. 115, 307-315.
[88] Xu, Z., Wang, F., Peng, L., Fang, X. and Cen, P. (2005) Appl. Biochem. Biotechnol. 120, 1-13.
[89] Sára, S. and Sleytr, U. (2000) J. Bacteriol. 182, 859-868.
[90] Wu, Z., Ericksen, B., Tucker, K., Lubkowski, J. and Lu, W. (2004) J Pept Res 64, 118-25.
[91] Ericksen, B., Wu, Z., Lu, W. and Lehrer, R. I. (2005) Antimicrob Agents Chemother 49, 269-75.
[92] Ouellette, A. J. (1999) Am J Physiol 277, G257-61.
[93] Ghosh, D. et al. (2002) Nat Immunol 3, 583-90.
[94] Porter, E. M., Bevins, C. L., Ghosh, D. and Ganz, T. (2002) Cell Mol Life Sci 59, 156-70.

That which is claimed is:

1. A delivery device for administering a therapeutic agent to intestinal epithelium in a subject comprising:
   a native defensin or analog thereof encapsulated in a biodegradable microsphere comprising poly(DL-lactide-co-glycolide); and
   a coating attached to the biodegradable microsphere consisting of the bacterium surface layer protein SlpA purified from *Lactobacillus brevis*, wherein said SlpA is self-assembling, and has affinity for and is accessible for binding with the intestinal epithelium.

2. The delivery device of claim 1 wherein the defensin is HD5a or an analog thereof.

3. The delivery device of claim 1, in a pharmaceutically acceptable carrier.

4. The delivery device claim 3, wherein the device is provided in the form of a unitary dosage unit.

5. A method of preparing a delivery device for delivering a therapeutic agent to intestinal epithelium in a subject, the method comprising:
   encapsulating a native defensin or analog thereof in a biodegradable microsphere comprising poly(DL-lactide-co-glycolide), and coating the biodegradable microsphere with an outer layer consisting of the bacterium surface layer protein SlpA purified from *Lactobacillus brevis*, wherein said bacterium surface layer protein is self-assembling, and has affinity for and is accessible for binding with the intestinal epithelium.

6. The method of claim 5 wherein the defensin is HD5a or an analog thereof.

7. A method of treating Crohn's disease comprising administering to a subject a pharmaceutical formulation comprising the delivery device of claim 1.

* * * * *

UNITED STATES PATENT AND TRADEMARK OFFICE
CERTIFICATE OF CORRECTION

PATENT NO.       : 8,895,062 B2                    Page 1 of 1
APPLICATION NO.  : 12/162011
DATED            : November 25, 2014
INVENTOR(S)      : De Leeuw et al.

It is certified that error appears in the above-identified patent and that said Letters Patent is hereby corrected as shown below:

In the Specification

Column 1, remove --- lines 13-18 ---

Signed and Sealed this
Seventh Day of April, 2015

Michelle K. Lee
*Director of the United States Patent and Trademark Office*